United States Patent
Barbut

(10) Patent No.: US 7,452,352 B2
(45) Date of Patent: *Nov. 18, 2008

(54) METHODS FOR PREVENTING DISTAL EMBOLIZATION FROM THE VERTEBROBASILAR ARTERY USING FLOW REVERSAL

(75) Inventor: Denise R. Barbut, New York, NY (US)

(73) Assignee: CoAxia, Inc., Maple Grove, MN (US)

( * ) Notice: Subject to any disclaimer, the term of this patent is extended or adjusted under 35 U.S.C. 154(b) by 114 days.

This patent is subject to a terminal disclaimer.

(21) Appl. No.: 11/004,110

(22) Filed: Dec. 2, 2004

(65) Prior Publication Data

US 2005/0154298 A1 Jul. 14, 2005

Related U.S. Application Data

(62) Division of application No. 09/792,732, filed on Feb. 23, 2001, now Pat. No. 6,887,227.

(51) Int. Cl.
*A61M 31/00* (2006.01)
*A61M 29/00* (2006.01)

(52) U.S. Cl. .................................. 604/508; 604/96.01

(58) Field of Classification Search ................ 604/500, 604/507, 505, 506, 514
See application file for complete search history.

(56) References Cited

U.S. PATENT DOCUMENTS

| | | | |
|---|---|---|---|
| 4,413,989 A | 11/1983 | Schjeldahl et al. | |
| 4,531,943 A * | 7/1985 | Van Tassel et al. | 604/523 |
| 4,921,478 A | 5/1990 | Solano et al. | |
| 5,423,742 A | 6/1995 | Theron | |
| 5,749,890 A * | 5/1998 | Shaknovich | 606/198 |
| 5,765,568 A | 6/1998 | Sweezer, Jr. et al. | |
| 5,769,812 A | 6/1998 | Stevens et al. | |
| 5,833,645 A | 11/1998 | Lieber et al. | |
| 5,833,650 A | 11/1998 | Imran | |
| 5,910,154 A * | 6/1999 | Tsugita et al. | 606/200 |
| 5,938,645 A | 8/1999 | Gordon | |
| 6,146,370 A * | 11/2000 | Barbut | 604/500 |
| 6,231,551 B1 | 5/2001 | Barbut | |

(Continued)

OTHER PUBLICATIONS

Belli, "Percutaneous Transluminal Angioplasty" La Radiologiz Medica, Issue 76, 1998, pp. 174-178.*
Translation of Belli above.*

(Continued)

*Primary Examiner*—Kevin C. Sirmons
*Assistant Examiner*—Elizabeth R MacNeill
(74) *Attorney, Agent, or Firm*—O'Melveny & Myers LLP

(57) ABSTRACT

The invention provides a medical device having a catheter and one or more expandable constricting/occluding members. The catheter has a lumen communicating with a port at its distal end. The lumen and port are adapted for introduction of therapeutic or diagnostic devices, including an angioplasty/stent catheter and an atherectomy catheter, into a vertebral or basilar artery. The constrictor/occluder is mounted proximal to the port of the catheter. Manometers may be mounted distal to one or more constrictors for measuring pressure distal to the constrictor(s). Methods of using the devices for preventing distal embolization during vertebral and/or basilar procedures by reversing blood flow in the vertebral artery toward the subclavian artery are disclosed.

17 Claims, 22 Drawing Sheets

U.S. PATENT DOCUMENTS 6,582,448 B1 6/2003 Boyle et al.
6,595,980 B1 * 7/2003 Barbut .................. 604/509
6,676,683 B1 * 1/2004 Addis .................... 606/200
6,887,227 B1 * 5/2005 Barbut .................. 604/500

OTHER PUBLICATIONS

Theron, et al. "New Triple Coaxial Catheter System for Carotid Angioplasty with Cerebral Protection." American Journal of Radiology 11:869-74 (Sep./Oct. 1990).

* cited by examiner

METHODS FOR PREVENTING DISTAL EMBOLIZATION FROM THE VERTEBROBASILAR ARTERY USING FLOW REVERSAL

This is a divisional of U.S. application Ser. No. 09/792,732, now U.S. Pat. No. 6,887,227, filed Feb. 23, 2001, which is hereby expressly incorporated by reference in its entirety.

FIELD OF THE INVENTION

The present invention relates generally to devices and methods useful in treating patients with stroke or occlusive cerebrovascular disease. More specifically, the invention provides an extracranial device capable of reversing flow down a vertebral or basilar artery, and into the innominate, subclavian, or brachial artery during an invasive procedure, thereby avoiding distal embolization of vascular debris. Various diagnostic or therapeutic instruments, including an atherectomy catheter, a filter, and/or an angioplasty/stent catheter, can be introduced through or in combination with the device for treating the vertebrobasilar occlusion. The invention may also be useful to reverse flow during a stroke.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Outcome following stroke is influenced by a number of factors, the most important being the nature and severity of the resulting neurologic deficit. Overall, less than 80% of patients with stroke survive for at least 1 month, and approximately 35% have been cited for the 10-year survival rates. Of patients who survive the acute period, up to 75% regain independent function, while approximately 15% require institutional care.

The majority of the strokes are caused by occluded vessels that deprive the brain of oxygen-carrying blood. The vertebral and basilar arteries typically provide blood supply to the brainstem, the cerebellum, and the posterior cerebrum. Infarction in these areas of the brain can produce dire consequences. For example, basis pontis infarction due to basilar artery occlusion may lead to a "locked-in state" characterized by quadriplegia and paralysis of the bulbar muscle such that the patient can only communicate by moving eyes or eyelids. Dysfunction of the reticular activating system, which controls autonomic function of vital body organs, e.g., the cardiac and respiratory function, may lead to coma or death. Ischemia caused by vertebrobasilar insufficiency often produces multifocal lesions including a considerable longitudinal extent of the brain stem, thereby giving rise to a combination of symptoms, including dizziness, double vision, facial weakness, and gait instability.

Current treatments for patients with ischemia or infarction in the territory of the vertebral or the basilar artery include anticoagulation, e.g., heparin, and supportive care. Recently, vertebral thromboatherectomy, percutaneous angioplasty, and stenting are increasingly performed to remove the occluding lesions. However, the main complication of these procedures is distal embolization of atheromatous material downstream of the vertebral artery being treated, causing stroke in the posterior circulation.

New devices and methods are thus needed in patients undergoing invasive procedures for definitive or prophylactic treatment of occluding lesions in the vertebrobasilar circulation, thereby minimizing the risk of distal embolization to prevent ischemic stroke.

SUMMARY OF THE INVENTION

The invention provides devices and methods for preventing ischemic stroke in patients undergoing invasive vertebrobasilar procedures, including angioplasty, stent placement, and/or filter insertion, by reversing blood flow down a vertebral artery being treated. In this way, embolic debris generated as a result of placing instrumentation within a diseased vertebrobasilar artery is diverted into the innominate, subclavian, or brachial artery, thereby preventing stroke by minimizing distal embolization to the narrow posterior cerebral vessels. The devices and methods are also useful to remove an embolus and improve flow (by reversing collateral blood flow across the circle of Willis) in patients with acute stroke.

The invention utilizes devices comprising a catheter having one or two expandable constricting members at its distal end. Each constrictor may be a balloon, in certain cases a toroidal balloon, or a device of any other appropriate shape, so that it can fully or partially occlude blood flow. The lumen of the catheter may be adapted for insertion of a therapeutic instrument, such as an angioplasty, atherectomy, and/or stent catheter. A manometer is optionally mounted proximal and/or distal to the constricting member for monitoring blood pressure proximal and/or distal the constrictor.

The occluder/constrictor is mounted near the distal end of the catheter, in certain cases proximal to a port. Each of the balloon occluder and constrictor communicates with an inflation lumen and an inflation port at the proximal end of the catheter. In certain embodiments, the catheter will include first and second constriction/occlusion members. The second constrictor is mounted on a second member which is slidably insertable through the catheter, and passes beyond the first constrictor. In this way, the second member and the second constrictor are moveable longitudinally relative to the first constrictor. In other embodiments, the constrictor may consist of a balloon having more than one opening at its center for the passage of blood, or may consist of more than one expandable balloons allowing passage of blood through the gap between the arterial wall and the expanded balloons. The proximal end of the catheter may include a hemostatic valve.

In still another embodiment, the catheter includes a second lumen communicating with a proximal end and an infusion port at its distal end. The port is located distal to the distal port of the catheter. The second lumen and its port are adapted for delivering a pharmaceutical agent to the vertebral artery, including an angiographic dye.

In still another embodiment, the constrictor includes a shunt for the passage of blood therethrough. The shunt comprises a tube having a lumen communicating with a proximal end and a distal end. Any device described in Barbut, U.S. Pat. No. 6,146,370, incorporated herein by reference in its entirety, may also be used in the methods described herein.

The invention provides methods for reversing flow in a vertebrobasilar artery where an invasive procedure is to be performed in the vertebral or basilar artery. More specifically, the methods are useful in reversing flow down the occluded vertebral or basilar artery and into the innominate, subclavian, or brachiocephalic artery.

In a first method using the devices described above, a technique for treating a vertebral artery stenosis or dissection without risk of distal embolization is provided. A distal end of the catheter is inserted into the left or right subclavian artery in a retrograde or antegrade direction through an incision made on a peripheral artery, such as the brachial, the femoral artery, the subclavian artery, or the brachiocephalic artery. A constricting member carried at the distal end of the catheter is located in the unilateral subclavian artery upstream the vertebral artery in which flow reversal is desired. The constricting member is expanded to constrict or occlude the subclavian or innominate artery. This results in progressive reduction of blood pressure downstream of the constrictor, which ultimately results at a critical pressure level in reversal of blood flow from the higher-pressure vertebral artery to the lower-pressure innominate, subclavian, and/or brachiocephalic artery. The flow reversal can be verified fluoroscopically with dye. In certain methods, the lesion within the vertebral artery is then treated by advancing a therapeutic instrument into the unilateral vertebral artery to reduce the stenosis. The embolic debris generated during the procedure will flow toward the innominate, subclavian, and/or brachiocephalic artery and arteries of the extremity, thereby preventing stroke from distal vertebral embolization.

In another method, flow reversal within a vertebral artery is achieved by inserting the distal end of the catheter into the vertebral artery. The constricting member is located and expanded within the vertebral artery to partially occlude the vertebral artery proximal or distal to the lesion. Blood flow is thereby reversed from the high-pressure vertebral to the low-pressure innominate, subclavian, and/or brachiocephalic artery. The lesion within the vertebral artery may then be treated as described above.

In another method, for reversing blood flow within a vertebral artery, the catheter is inserted into the subclavian artery and the constricting member is located in the brachiocephalic trunk upstream of the vertebral artery in which flow reversal is sought. Blood flow is thereby reversed from the high-pressure vertebrobasilar junction to the low-pressure subclavian artery. The lesion within the vertebral artery may then be treated as described above.

In another method, flow reversal within a basilar artery is accomplished. In this method, the distal end of a catheter is inserted into either vertebral artery. The constricting member is then located in the vertebral artery and expanded to partially occlude the vertebral artery. This procedure will result in reversal of blood flow of high-pressure circle of Willis to the low-pressure vertebrobasilar junction. Alternatively, one constricting member is located in a first vertebral artery and expanded to partially or fully occlude the first vertebral artery, and a second constricting member is located in a second vertebral artery and expanded to partially or fully occlude the second vertebral artery. In a further alternative method, one constricting member is located in a first vertebral artery and expanded to partially or fully occlude the first vertebral artery, and a second constricting member is located in the contralateral subclavian artery and expanded to partially or fully occlude the contralateral subclavian artery. In a further alternative method, one constricting member is located in the right brachiocephalic or subclavian artery and expanded to partially or fully occlude the right brachiocephalic or subclavian artery, and a second constricting member is located in the left subclavian artery and expanded to partially or fully occlude the left subclavian artery.

It will be understood that there are several advantages in using the devices and methods disclosed herein for prevention of distal embolization during use of instrumentation in the vertebral or basilar artery. For example, the devices (1) abolish the need for suction distal to the vertebrobasilar occlusion, thereby minimizing blood loss, (2) eliminate the need for systemic anticoagulation, pumping, and a second arterial or venous stick, all of which are required where suction is employed, (3) can be used to introduce a variety of diagnostic or therapeutic instrument to the vertebrobasilar artery, (4) can be used in any procedures which require instrumentation within the vertebrobasilar artery, (5) can be used for definitive treatment of acute or subacute ischemic stroke or stroke prevention, (6) can be used in the angiogram or fluoroscopy suite available in most hospitals, and (7) require only one incision site for entry.

DETAILED DESCRIPTION

The cerebral circulation is regulated in such a way that a constant total cerebral blood flow (CBF) is generally maintained under varying conditions. For example, a reduction in flow to one part of the brain, such as in stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation via the Circle of Willis.

Figure 1:
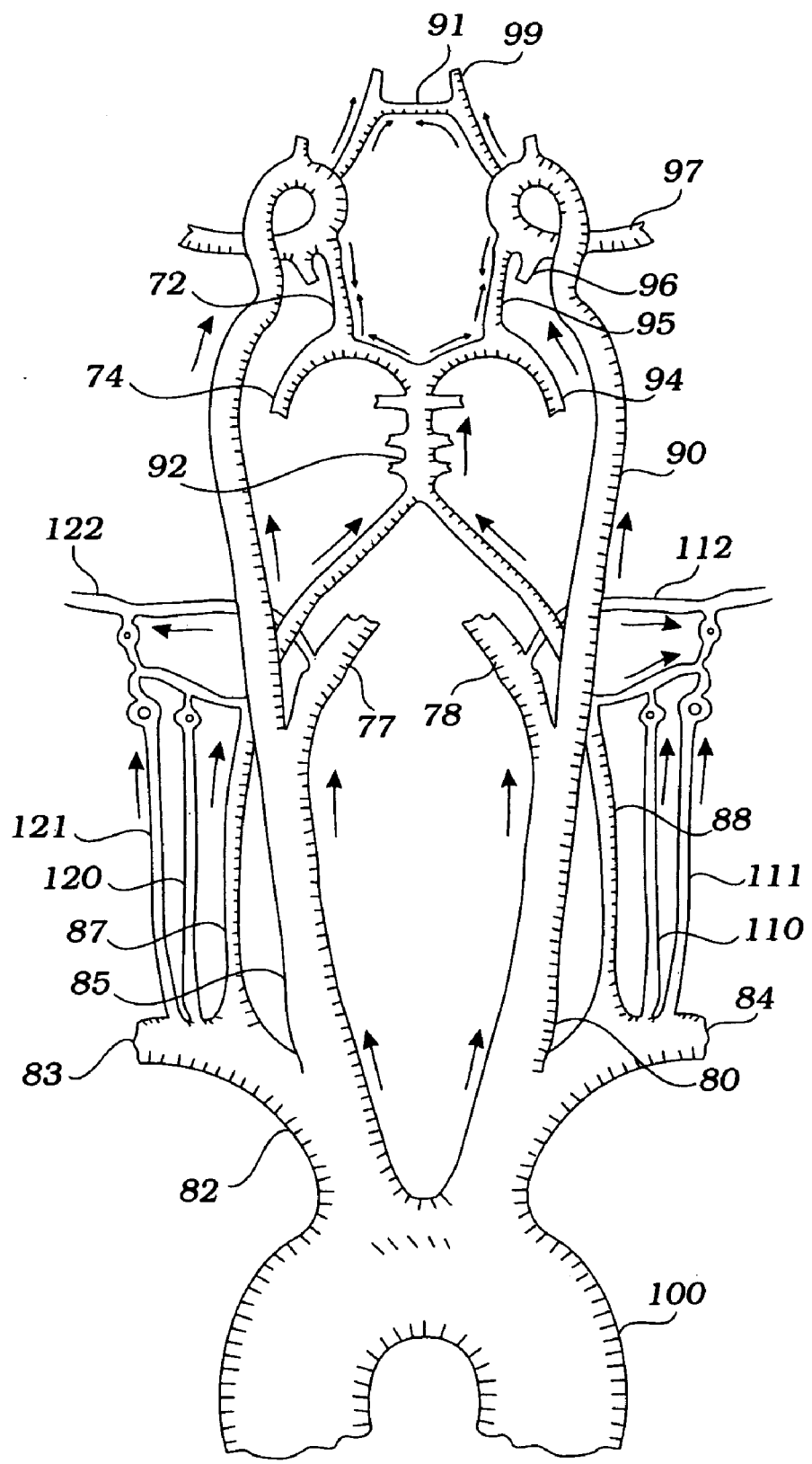
FIG. 1 depicts normal collateral circulation in the Circle of Willis and the posterior circulation.

FIG. 1 depicts normal cerebral circulation and collateral blood flow in the Circle of Willis and the posterior circulation. Aorta 100 gives rise to right brachiocephalic trunk 82, left common carotid artery (CCA) 80, and left subclavian artery 84. The brachiocephalic artery further branches into right common carotid artery 85 and right subclavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect respectively with right posterior cerebral artery (PCA) 74 and left PCA 94. The two posterior communicating arteries and PCAs, and the origin of the posterior cerebral from basilar artery 92 complete the circle posteriorly.

Right subclavian artery 83 gives rise to right vertebral artery 87, tight anterior cervical artery 120, and right thyrocervical artery 121. Similarly, left subclavian artery 84 gives rise to left vertebral artery 88, left anterior cervical artery 110, and left thyrocervical artery 111. The left CCA also gives rise to external carotid artery (ECA) 78, which branches extensively to supply most of the structures of the head except the brain and the contents of the orbit. Right occipital artery 122, a branch of right ECA 77, communicates with right vertebral artery 87, right anterior cervical artery 120, and right thyrocervical artery 121 to form the right posterior collateral circulation. Similarly, left occipital artery 112, a branch of left ECA 78, communicates with left vertebral artery 88, left anterior cervical artery 110, and left thyrocervical artery 111 to form the left posterior collateral circulation.

Figure 2:
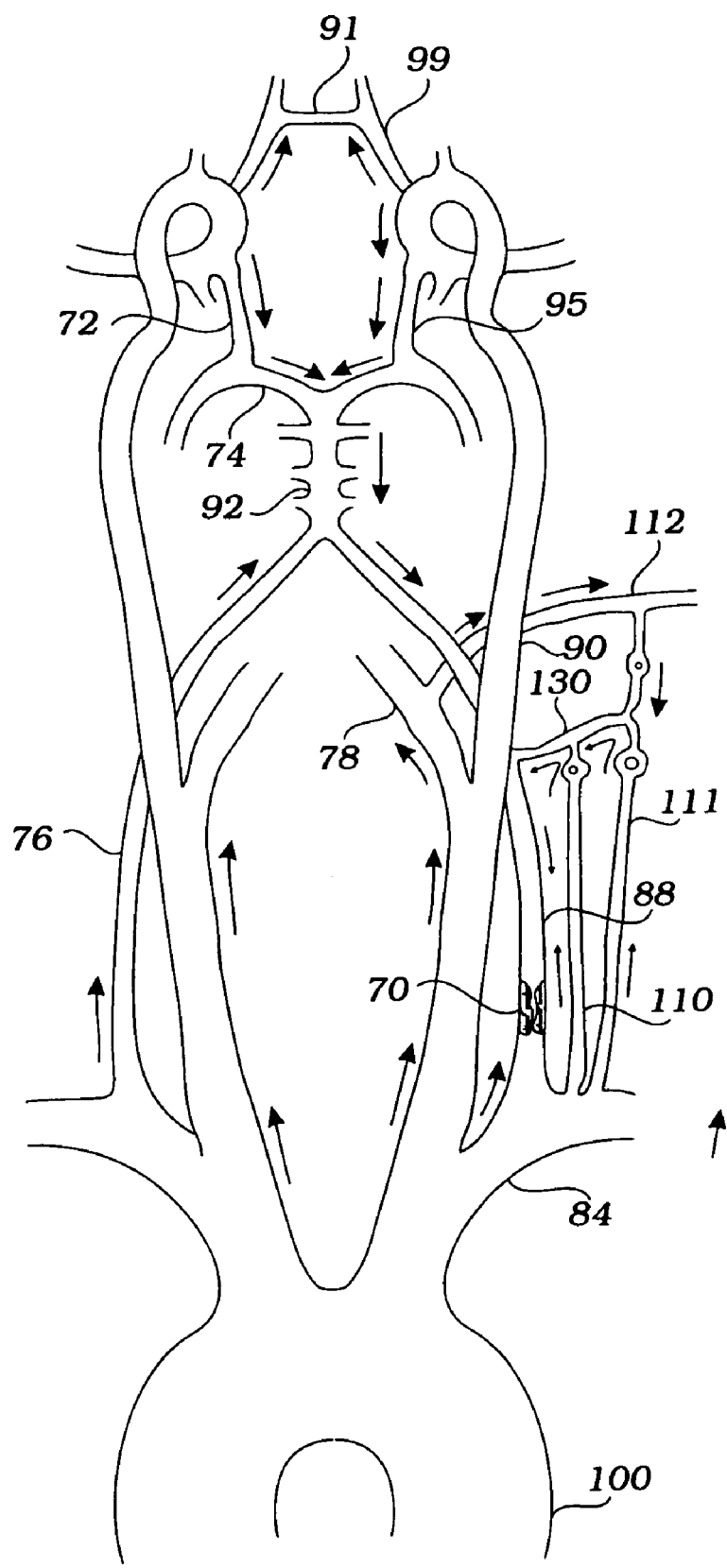
FIG. 2 depicts a reversed circulation in the Circle of Willis and the posterior circulation to compensate for an occlusion in the left vertebral artery.

When occluding lesion 70 occurs acutely, for example, in left vertebral artery 88, as depicted in FIG. 2, blood flow in the left cerebral artery, left external carotid artery 78, and right vertebral artery 76 increases, resulting in a directional change of flow through the Circle of Willis down basilar artery 92 to compensate for the sudden decrease of blood flow in the left vertebral artery. Specifically, blood flow reverses in right posterior communicating artery 72, right PCA 74, and left posterior communicating artery 95. Although main collateral blood flow to the left vertebral artery occurs through the right vertebral artery and the Circle of Willis, blood flow may also reverse in communicating branch 130 of left vertebral artery 88 with the left occipital artery, left anterior cervical artery, and left thyrocervical artery. The collateral blood flow through the posterior collateral circulation becomes important when the right vertebral artery is atretic.

When an occlusion occurs in the basilar artery (not shown), blood flow in the right and left cerebral arteries, internal carotid arteries, and external carotid arteries increases, resulting in a directional change of flow through the Circle of Willis down the basilar artery to compensate for the sudden decrease of blood flow. Specifically, blood flow reverses in right and left posterior communicating arteries, and right and left PCA's.

Figure 3A:
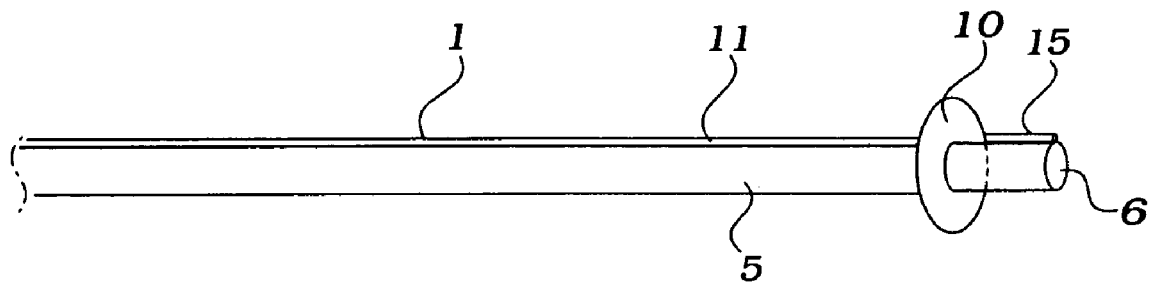
FIG. 3A depicts a distal region of an embodiment of the medical device having an occluding member for prevention of acute stroke during use of instrumentation in a vertebrobasilar artery.

Balloon catheters for achieving flow reversal in carotid arteries were described in Barbut, U.S. Pat. No. 6,146,370, incorporated herein by reference in its entirety. FIG. 3A depicts one embodiment of the device for preventing distal embolization during carotid instrumentation. The device comprises catheter 1 and balloon occluder 10. The catheter has lumen 5 communicating with a proximal end and port 6 at a distal end. The lumen and port are adapted for introduction of therapeutic or diagnostic instruments, e.g., atherectomy catheter, angioplasty catheter, and stent, to a carotid artery. Balloon occluder 10, communicating with inflation lumen 11, is mounted on the distal end of the catheter proximal to port 6. Manometer 15 is mounted distal to occluder 10 for monitoring blood pressure downstream the occluder.

Figure 3B:
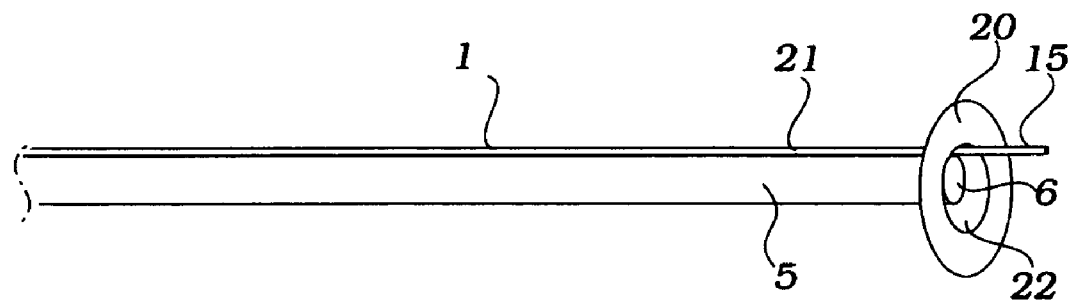
FIG. 3B depicts a distal region of another embodiment of the medical device having a constricting member.

FIG. 3B depicts another embodiment of the device having constricting member 20 mounted on a distal region of the catheter proximal to port 6. Constricting member 20 communicates with inflation lumen 21. The constrictor has central opening 22 which allows passage of blood. Manometer 15 is mounted distal to occluder 10 for monitoring blood pressure downstream the occluder.

Figure 4A:
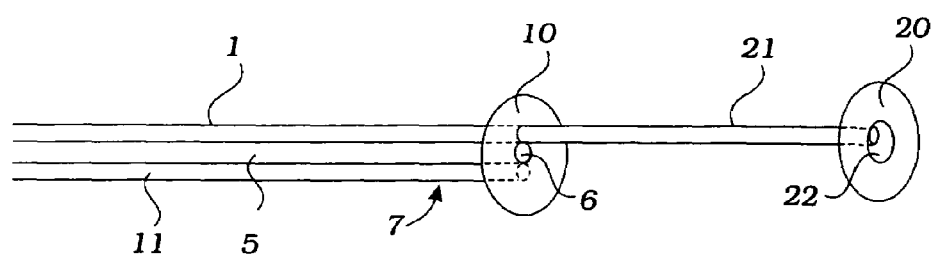
FIG. 4A depicts a distal region of another embodiment of the medical device having a constricting member distal an occluding member.

FIG. 4A depicts another embodiment of the device comprising catheter 1, balloon occluder 10, and constrictor 20. Lumen 5 of the catheter communicates with port 6 at distal end 7. The lumen and port are adapted for introduction of therapeutic or diagnostic instruments. Balloon occluder 10, communicating with inflation lumen 1 1, is mounted on the distal end of the catheter proximal to port 6. Balloon constrictor 20, communicating with inflation lumen 21, is mounted distal to port 6 and first occluder 10. The constrictor has central opening 22 which allows passage of blood. Inflation lumen 21 is an elongate member which, in certain embodiments, is slidably inserted through catheter 1, and is moveable longitudinally relative to catheter 1 and occluder 10.

Figure 4B:
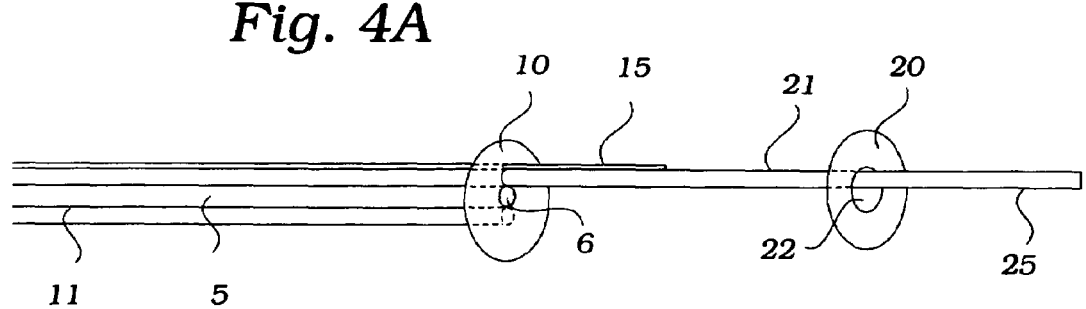
FIG. 4B depicts a distal region of another embodiment of the device having two manometers.

FIG. 4B depicts another embodiment of the device having two manometers. Manometer 15 is mounted distal to occluder 10 for measuring blood pressure between the occluder and the constrictor. Manometer 25 is mounted distal to constrictor 20 for measuring blood pressure downstream from constrictor 20.

Figure 5:
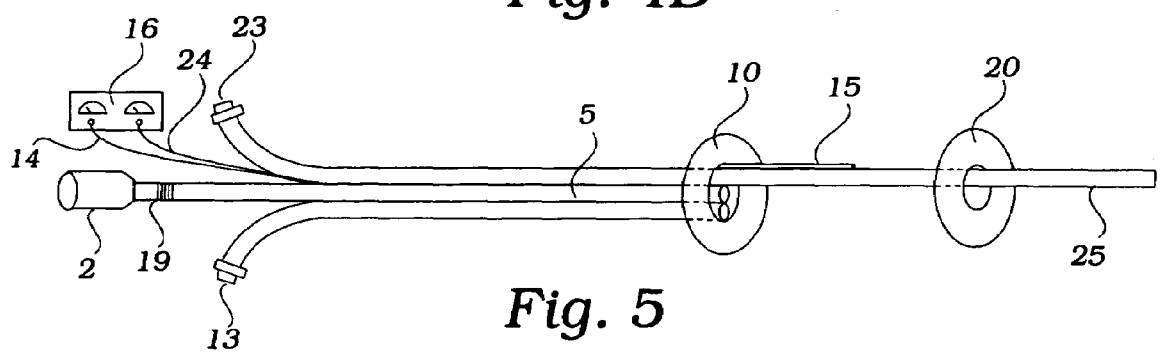
FIG. 5 depicts the device of FIG. 4B including a hemostatic valve at its proximal end.

In FIG. 5, proximal ends 14 and 24 of respective manometers 15 and 25 are connected to pressure monitor 16 for measuring blood pressure proximal and distal the constrictor. Inflation ports 13 and 23 communicate, respectively, with inflation lumens 11 and 21 for expanding balloon occluder 10 and constrictor 20. Lumen 5 of the catheter communicates with proximal end 2 which includes hemostatic valve 19.

Figure 6:
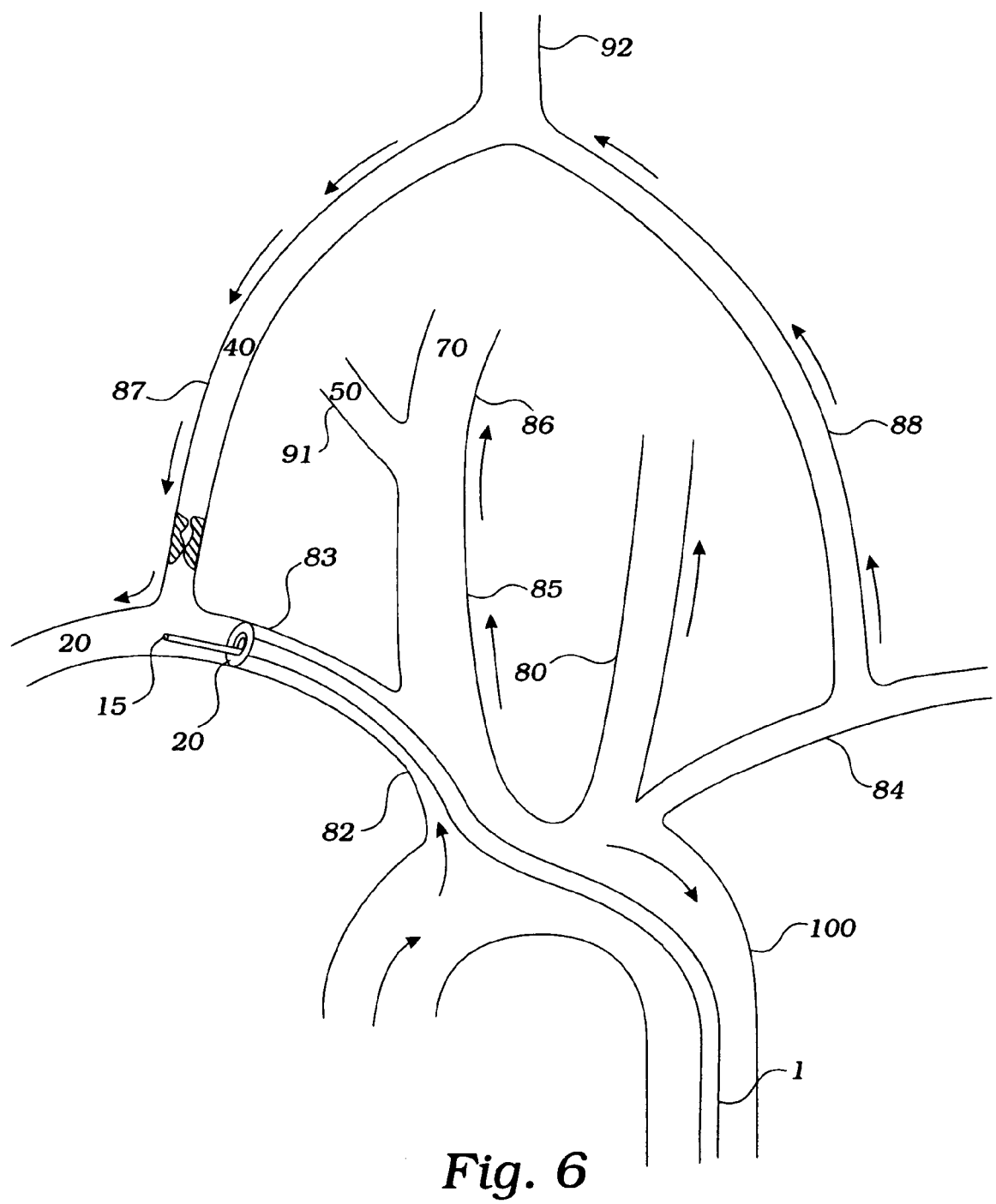
FIG. 6 depicts the device of FIG. 3B inserted in the right subclavian artery for treating a right vertebral artery occlusion.

In using the device of FIG. 3B to treat a right vertebral artery occlusion, a percutaneous incision is made on a peripheral artery, such as the femoral artery. A guide wire is inserted through the incision into the right subclavian artery in an antegrade direction and the distal end of the catheter is inserted over the guide wire so that constrictor 20 is positioned in right subclavian artery upstream the takeoff of the right vertebral artery as depicted in FIG. 6. Alternatively, the device is inserted through an incision in the right brachial artery and advanced into the right subclavian artery in a retrograde direction. The guide wire is then removed from the catheter.

Constricting member 20 is slowly expanded through its inflation lumen to constrict or occlude subclavian artery 83, causing progressive decline in the blood pressure of the subclavian artery downstream the constrictor. The pressure in the subclavian artery distal to the constrictor can be measured by manometer 15. The pressure distal to the constrictor is reduced, typically at approximately 20 mmHg, to create a favorable pressure gradient between the occluded right vertebral artery (typically having a pressure of 40 mmHg distal to the occlusion) and the subclavian artery to cause blood flow to reverse into the subclavian artery. The reversal of blood flow down the vertebral artery into the subclavian artery can be verified fluoroscopically with dye. After blood reversal is established, therapeutic devices, such as an atherectomy, angioplasty, and/or stenting catheter, can then be inserted through the lumen of the device, or through any other suitable percutaneous entry point, and advanced to treat the occluding lesion. With reversal of blood flow down the vertebral artery into the subclavian artery, distal embolization to the intracranial arteries is avoided, thereby minimizing risk of stroke. Distal embolization of the branches of the subvlavian artery that supply the extremity has far less devastating consequences than the arterial branches which supply the brain stem.

Figure 7:
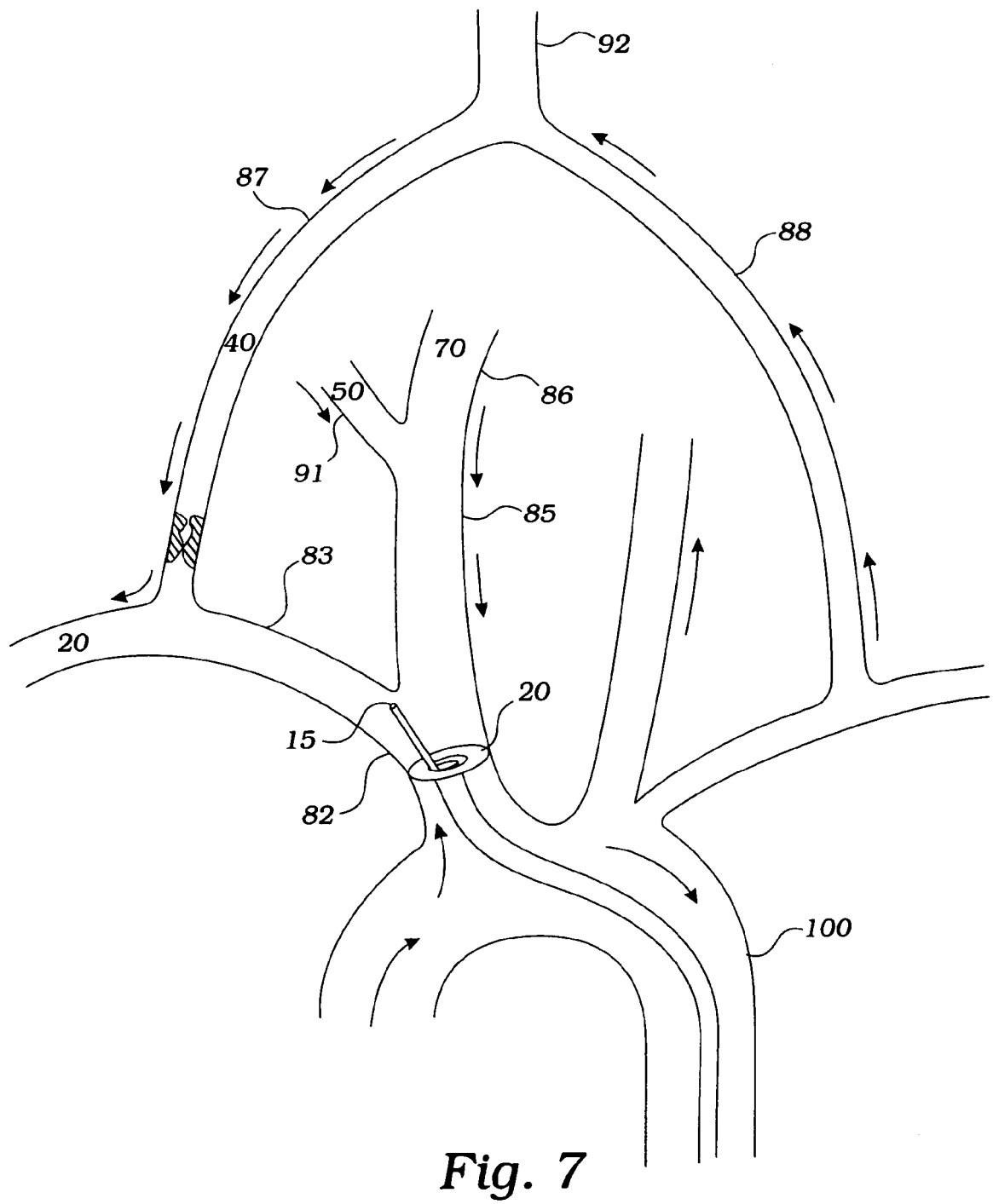
FIG. 7 depicts the device of FIG. 3B inserted in the right brachiocephalic artery for treating a right vertebral artery occlusion.

Flow reversal from the right vertebral artery having an occluding lesion down the ipsilateral subclavian artery can also be achieved by placing a constrictor or occluder in the ipsilateral brachiocephalic artery as shown in FIG. 7. The device of FIG. 3B is inserted and advanced into right brachiocephalic artery 82 upstream the takeoff of right common carotid artery 85. Constricting member 20 is slowly expanded, causing a reduction in the blood pressure (to approximately 20 mmHg) downstream the constrictor. As a result, a favorable pressure gradient is created between the right vertebral artery distal to the occluding lesion (typically having pressure of approximately 40 mmHg) and the subclavian artery, causing reversal of blood flow from the vertebral artery into the subclavian artery. Reversal of blood flow from right common carotid artery 85 into the subclavian artery also occurs due to the pressure differential between the CCA and the subclavian artery.

Figure 8:
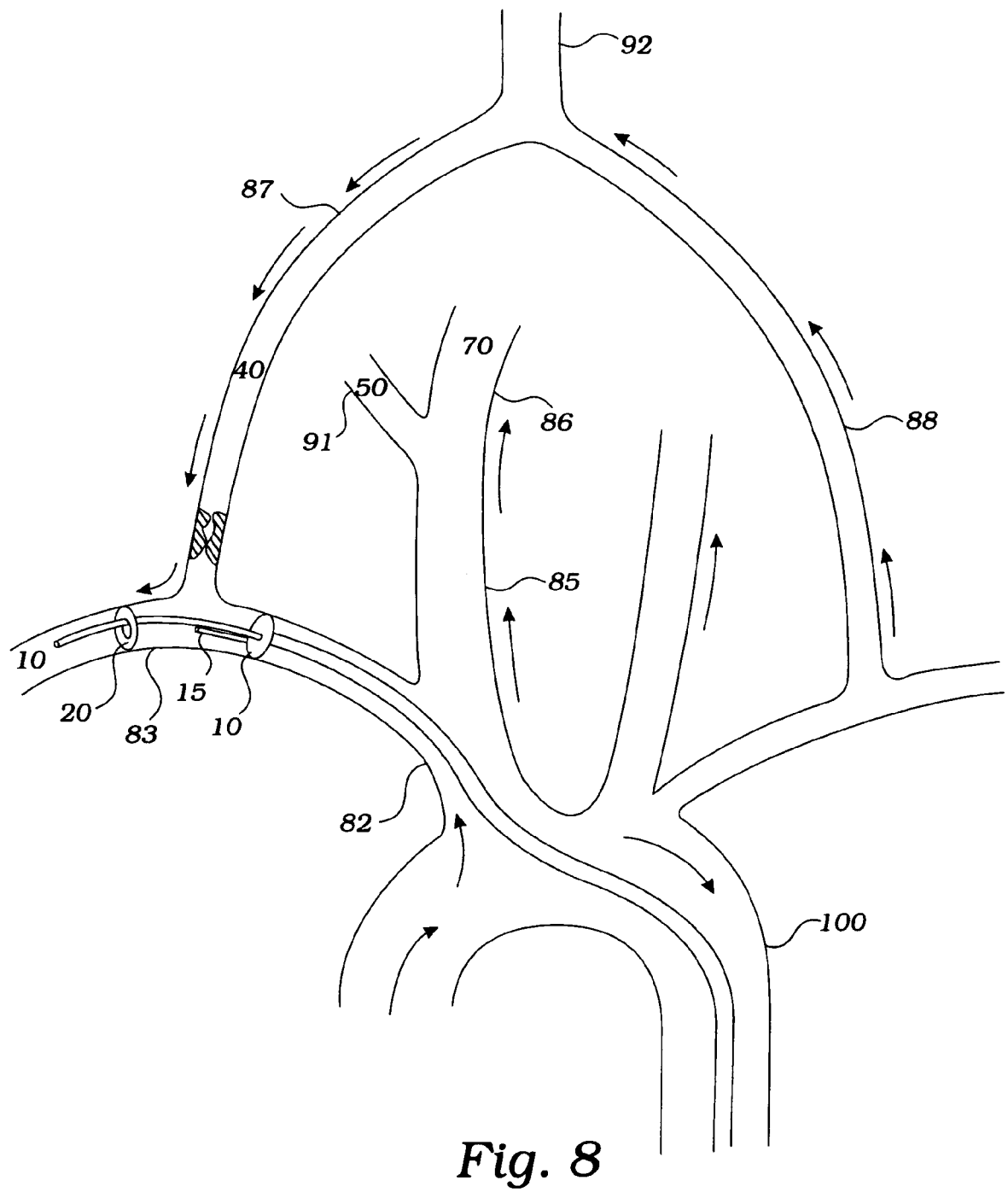
FIG. 8 depicts the device of FIG. 4B inserted in the right subclavian artery for treating a right vertebral artery occlusion.

In FIG. 8, the device of FIG. 4B is inserted in right subclavian artery 83 to further reduce pressure in the subclavian artery downstream the takeoff of right vertebral artery 87. Constricting/occluding member 10 is inserted and advanced in the subclavian artery downstream of the takeoff of right CCA 85 and constricting member 20 is advanced in the subclavian artery downstream of the takeoff of right vertebral artery 87. Constricting/occluding member 10 is first expanded to constrict/occlude the subclavian artery. If flow reversal dose not occur due to insufficient blood flow from the right vertebral artery, i.e., insufficient pressure gradient between the right vertebral artery and the subclavian artery, constricting/occluding member 20 is expanded to further reduce the pressure in the subclavian artery (to approximately 10 mmHg) to create a favorable pressure gradient to reverse blood flow into the subclavian artery from the vertebral artery.

Figure 8A:
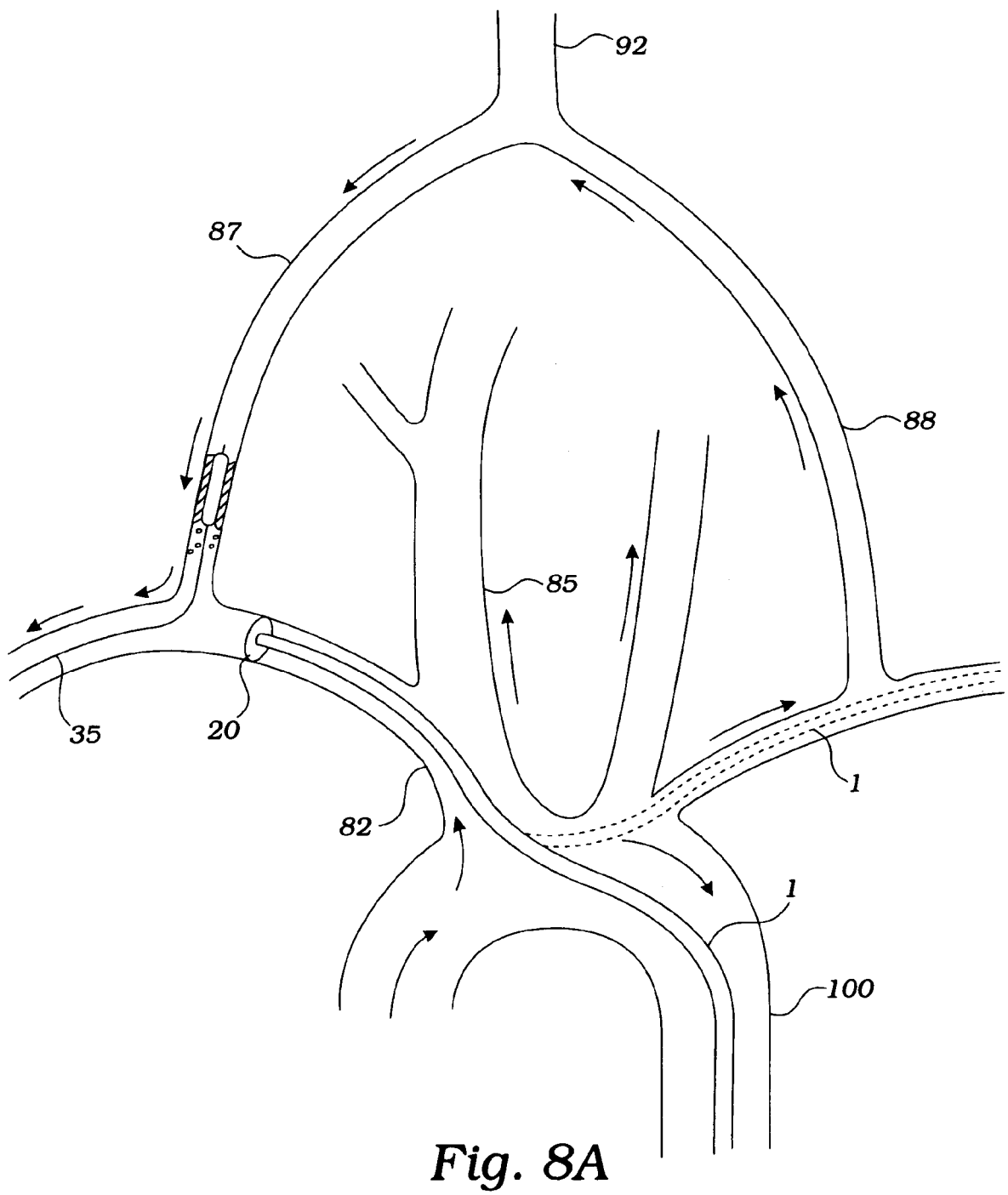
FIG. 8A depicts the device of FIGS. 3A or 3B inserted in the right subclavian artery for treating a right vertebral artery occlusion.

In FIG. 8A, a single constricting/occluding member 20 is placed and expanded in the right subclavian artery downstream of the takeoff of right CCA 85 and upstream of the takeoff of right vertebral artery 87. Catheter 1 can enter the body by femoral access or left subclavian access. Therapeutic catheter 35, here an angioplasty catheter, is inserted through the right subclavian artery and is advanced independently of catheter 1 to access the lesion in right vertebral artery 87. It will be understood that these devices and methods are applicable as well to treat lesions in the left vertebral artery.

Figure 8B:
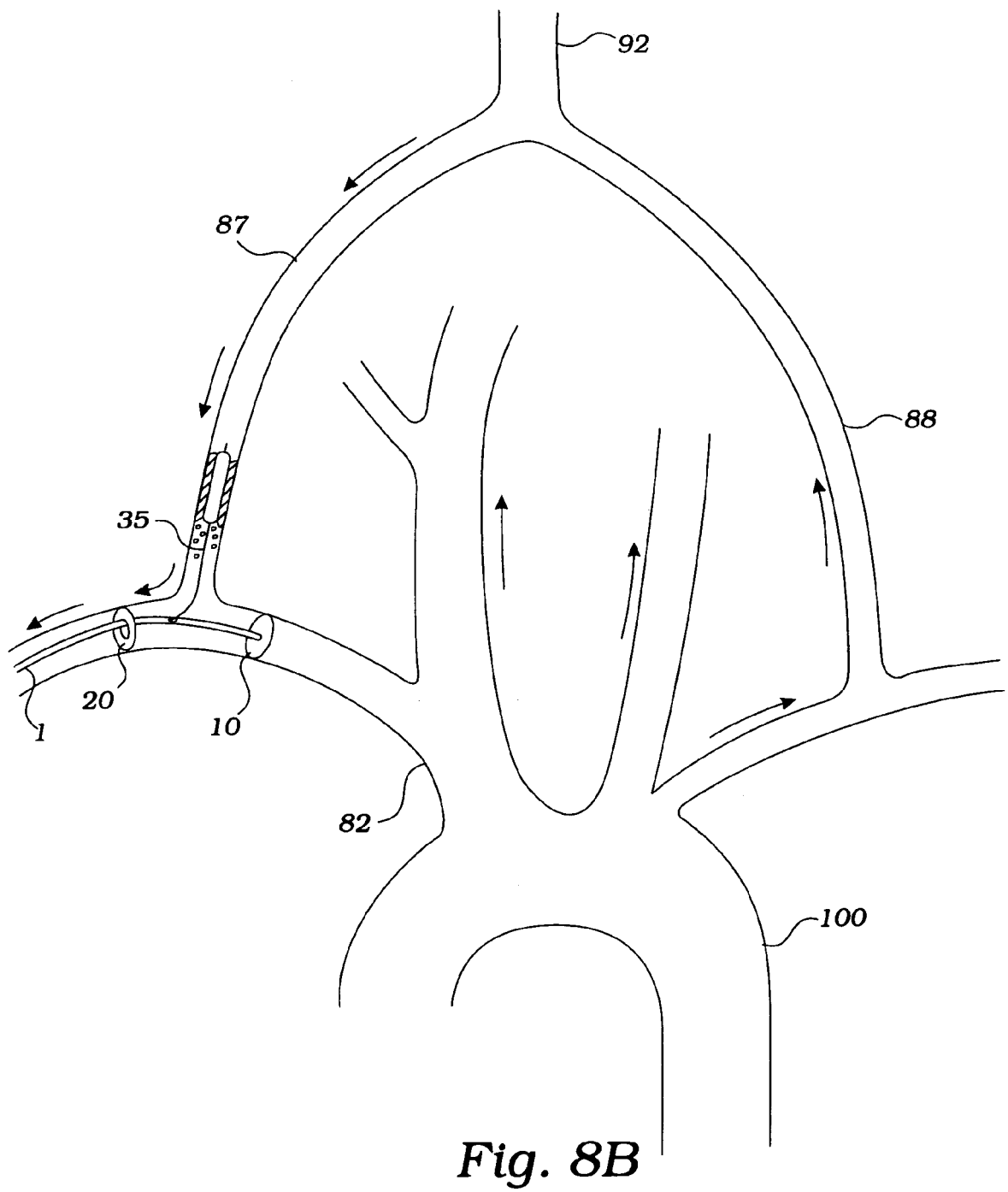
FIG. 8B depicts the device of FIG. 14A inserted in the right subclavian artery for treating a right vertebral artery occlusion.

In FIG. 8B, a first constricting/occluding member 20 is placed and expanded in the right subclavian artery downstream of the takeoff of right CCA 85 and upstream of the takeoff of right vertebral artery 87, and a second constricting/occluding member 10 is placed and expanded in the right subclavian artery downstream of the takeoff of right vertebral artery 87. Catheter 1 enters the body by right subclavian access. Therapeutic catheter 35, here an angioplasty catheter, is inserted through the right subclavian artery and through catheter 1 to access the lesion in right vertebral artery 87. It will be understood that these devices and methods are applicable as well to treat lesions in the left vertebral artery.

Figure 8C:
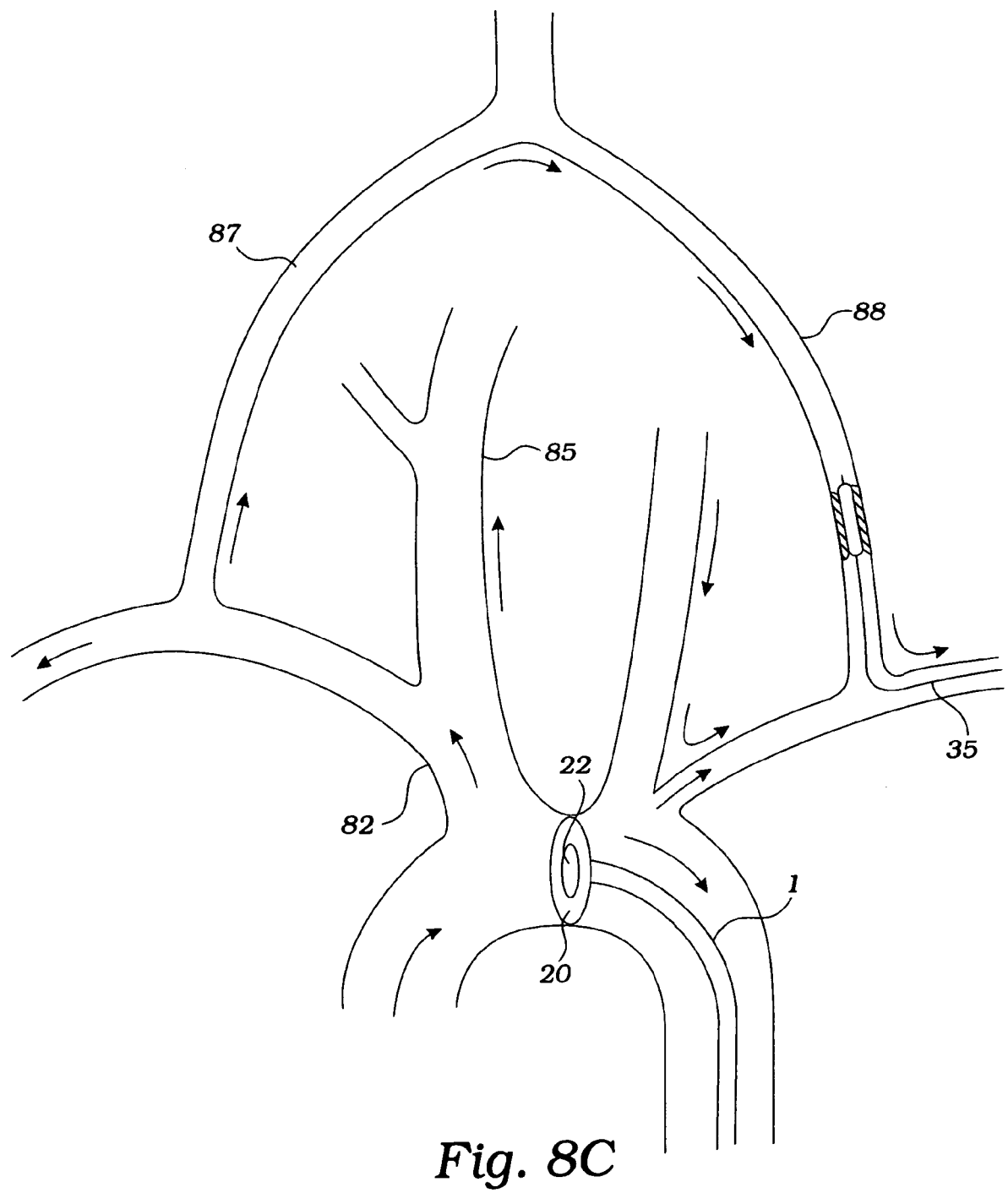
FIG. 8C depicts an aortic constriction catheter capable of causing flow reversal down the left vertebral artery for treating a left vertebral artery occlusion.

FIG. 8C depicts an aortic constriction catheter capable of causing flow reversal down the left vertebral artery for treating a left vertebral artery occlusion. Constricting member 20 is placed and expanded in the aorta downstream the brachiocephalic artery and upstream the left common carotid artery. Catheter 1 enters the body by femoral (shown in FIG. 8C), right subclavian, or left subclavian access. Therapeutic catheter 35, here an angioplasty catheter, is inserted through the left subclavian artery to access the lesion in left vertebral artery 87.

Figure 9:
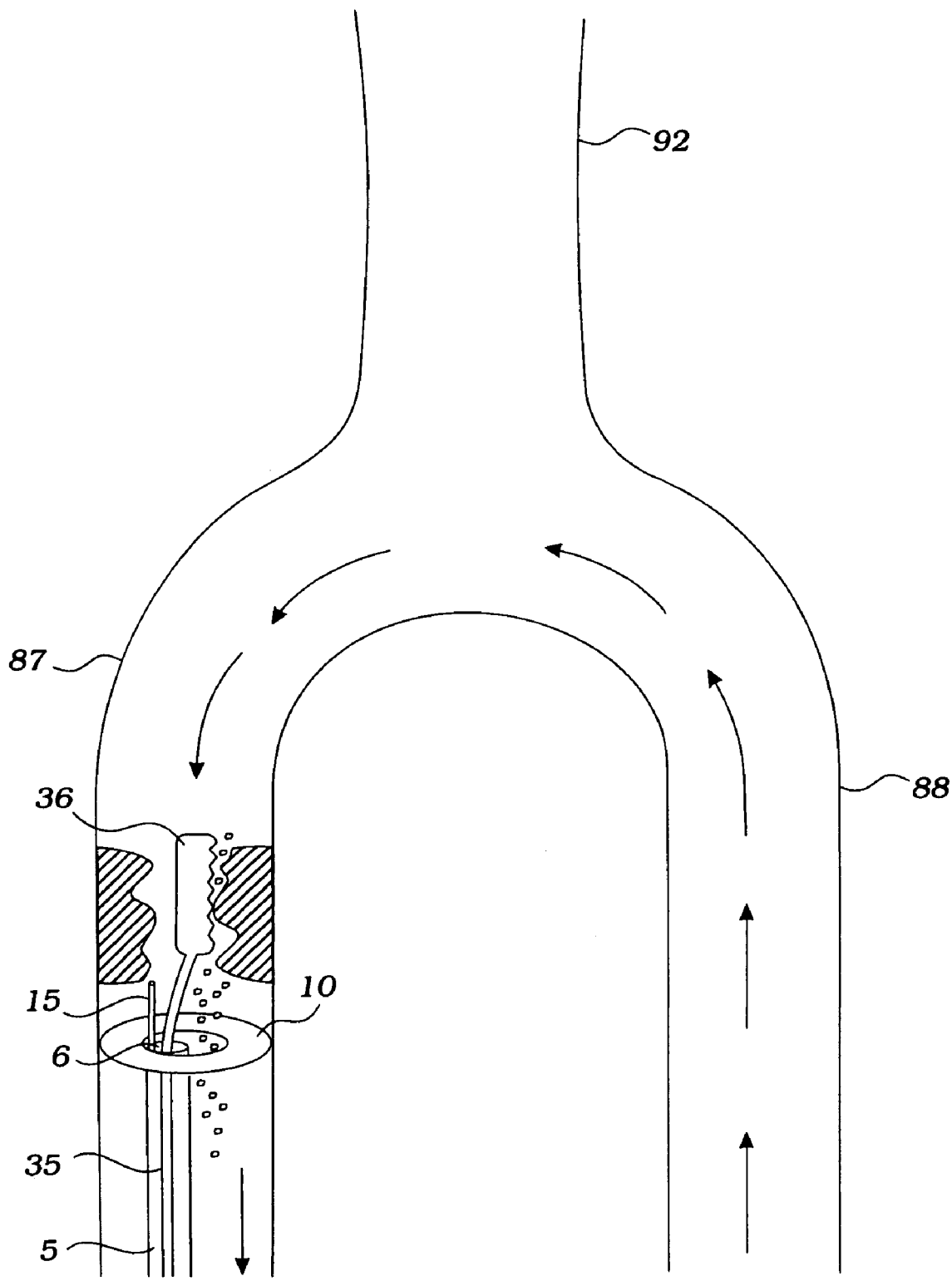
FIG. 9 depicts an atherectomy catheter introduced through the device of FIG. 3B in the right vertebral artery.

Reversal of blood flow down the vertebral artery being treated can also be accomplished by placing a constricting member proximal or distal to the occluding lesion in the vertebral artery. For example, in FIG. 9, a distal end of the device is inserted in an antegrade direction in right vertebral artery 87 and advanced proximal to the atheromatous lesion. Atherectomy catheter 35 is introduced through lumen 5 and port 6. After blood reversal is established in the vertebral artery across the atheromatous lesion by expanding constricting member 10, atherectomy device 36 is positioned over atheromatous lesion 70 and operated to remove the occluding lesion. The degree of constriction would be gradually increased until flow reversal confirmed by angiography is obtained. Embolic debris generated during the procedure is diverted from distal vertebral toward proximal vertebral artery and into the subclavian artery, thereby preventing distal embolization to the brain stem causing ischemic stroke. The construction of atherectomy catheters is well known in the art and will not be repeated in detail here. The reader is referred instead to Fischell, U.S. Pat. No. 5,409,454, Fischell, U.S. Pat. No. 4,898,575, Rydell, U.S. Pat. No. 4,857,045, Yock, U.S. Pat. Nos. 4,794,931, 5,000,185, and 5,313,949, Jang et al., U.S. Pat. No. 5,507,292, Farr, U.S. Pat. Nos. 4,950,277, 4,986,807, 5,019,088, Shiber, U.S. Pat. Nos. 4,894,051, 4,957,482, 4,979,939, 5,007,896, 5,024,651, 5,135,531, Summers, U.S. Pat. No. 5,087,265, Plassche et al., U.S. Pat. No. 5,318,576, Belknap, U.S. Pat. No. 5,366,464, Jang et al., U.S. Pat. No. 5,402,790, Mazur et al., Catherization and Cardiovascular Diagnosis 31:79-84 (1994), Fischell et al., U.S. Pat. Nos. 4,886,061, 5,100,425, and Barbut et al., U.S. Pat. No. 5,662,671, all of which are incorporated herein by reference as if fully set forth herein.

Figure 10:
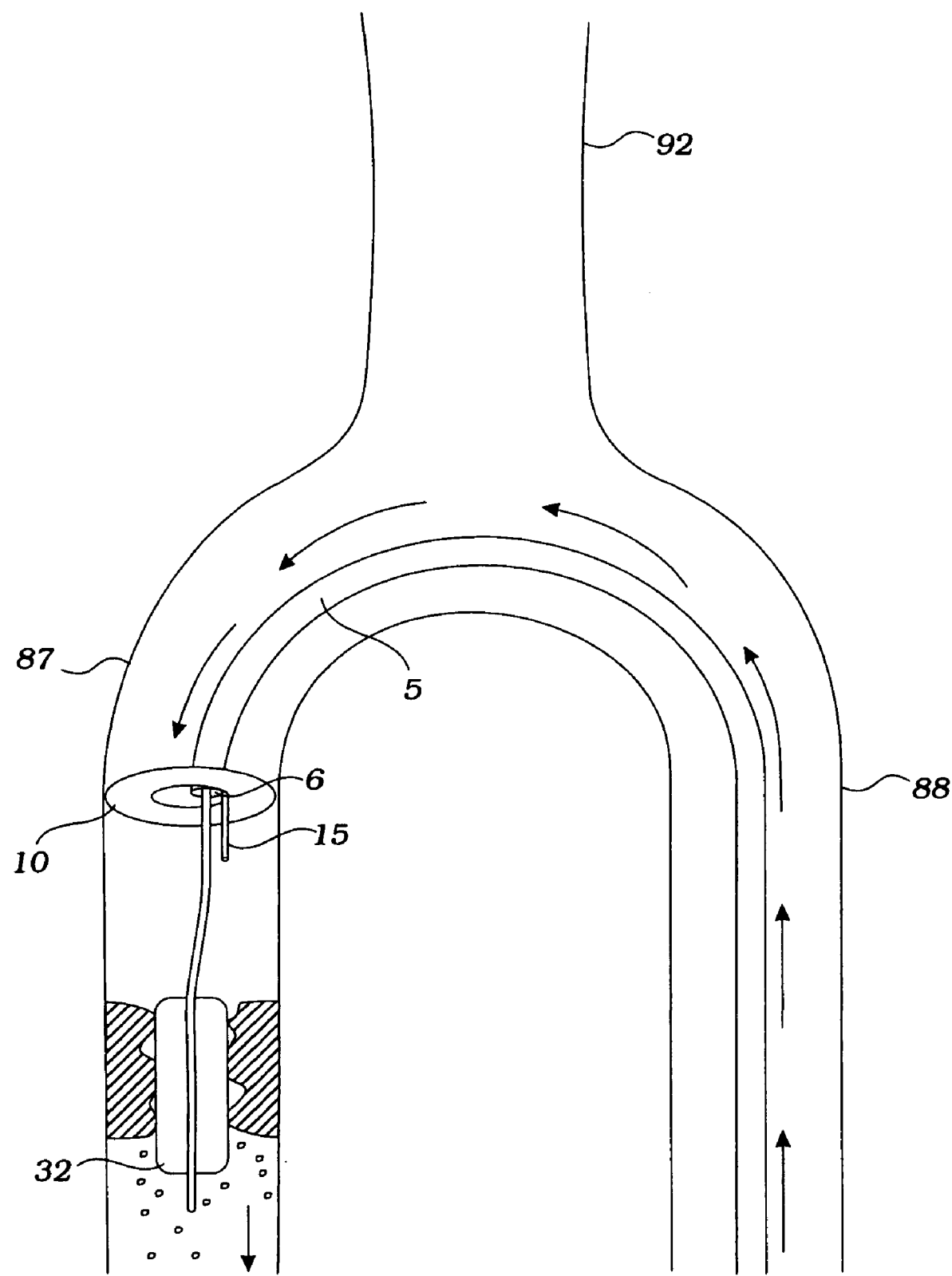
FIG. 10 depicts an angioplasty catheter introduced through the device of FIG. 3B in the right vertebral artery.
Figure 10A:
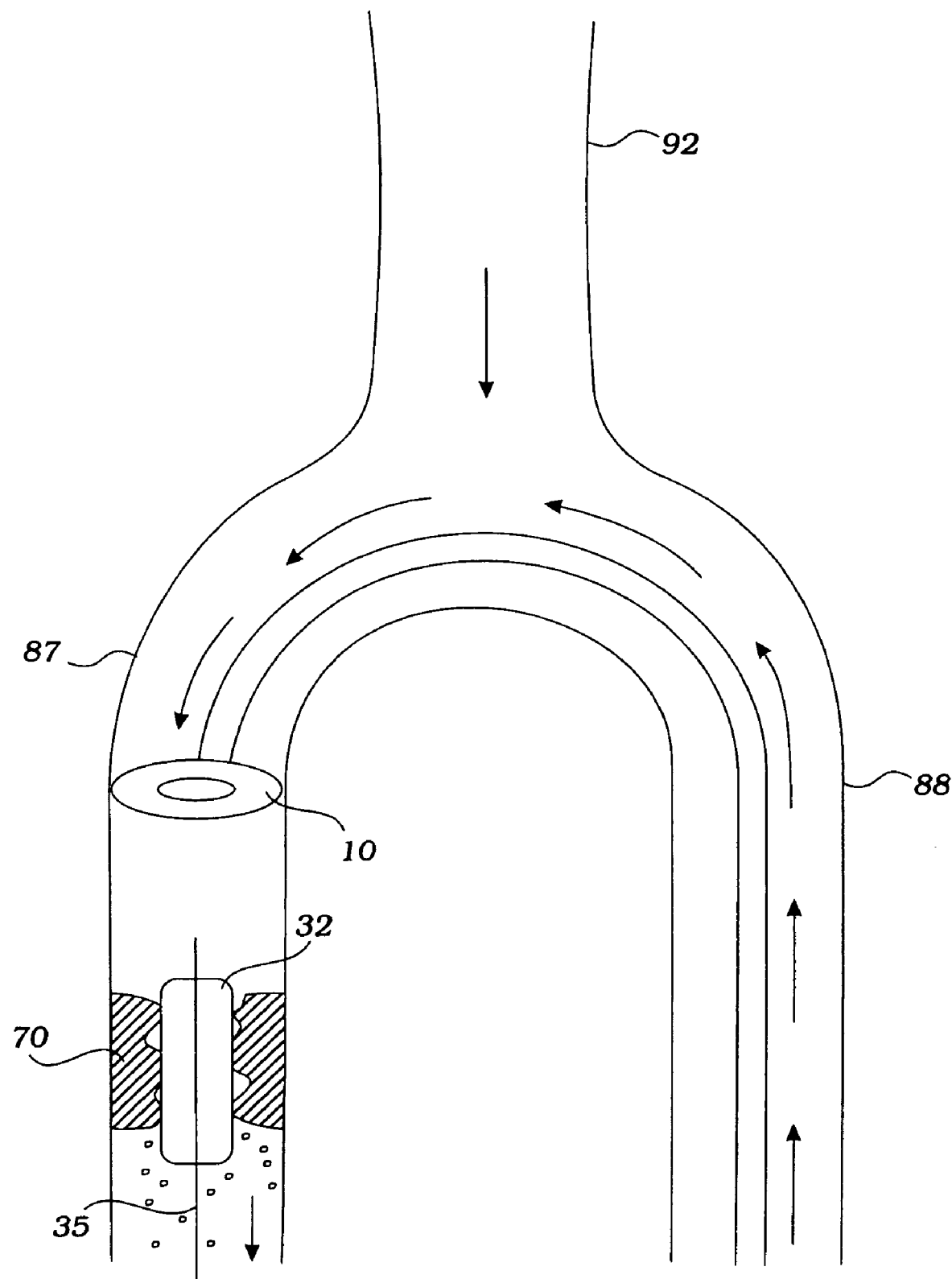
FIG. 10A depicts an angioplasty catheter introduced independent of the device of FIG. 3B in the right vertebral artery.

In FIG. 10, a distal end of the catheter is inserted in antegrade fashion through left vertebral artery 88 and in a retrograde fashion, into right vertebral artery 87 and the constrictor is located downstream of the atheromatous lesion. A catheter carrying angioplasty balloon 32 is inserted through lumen 5 and port 6. After flow reversal is established across the lesion by slowly expanding constricting member 10 and is verified using angiography, angioplasty balloon 32 is positioned over the atheromatous lesion and expanded to treat the lesion. Embolic debris generated during the procedure is diverted from the distal vertebral toward the proximal vertebral artery and into the subclavian artery, thereby preventing distal embolization to the brain stem causing ischemic stroke. Therapeutic catheter 35 may also be introduced independent of the constricting-occluding catheter, as shown in FIG. 10A.

Figure 11:
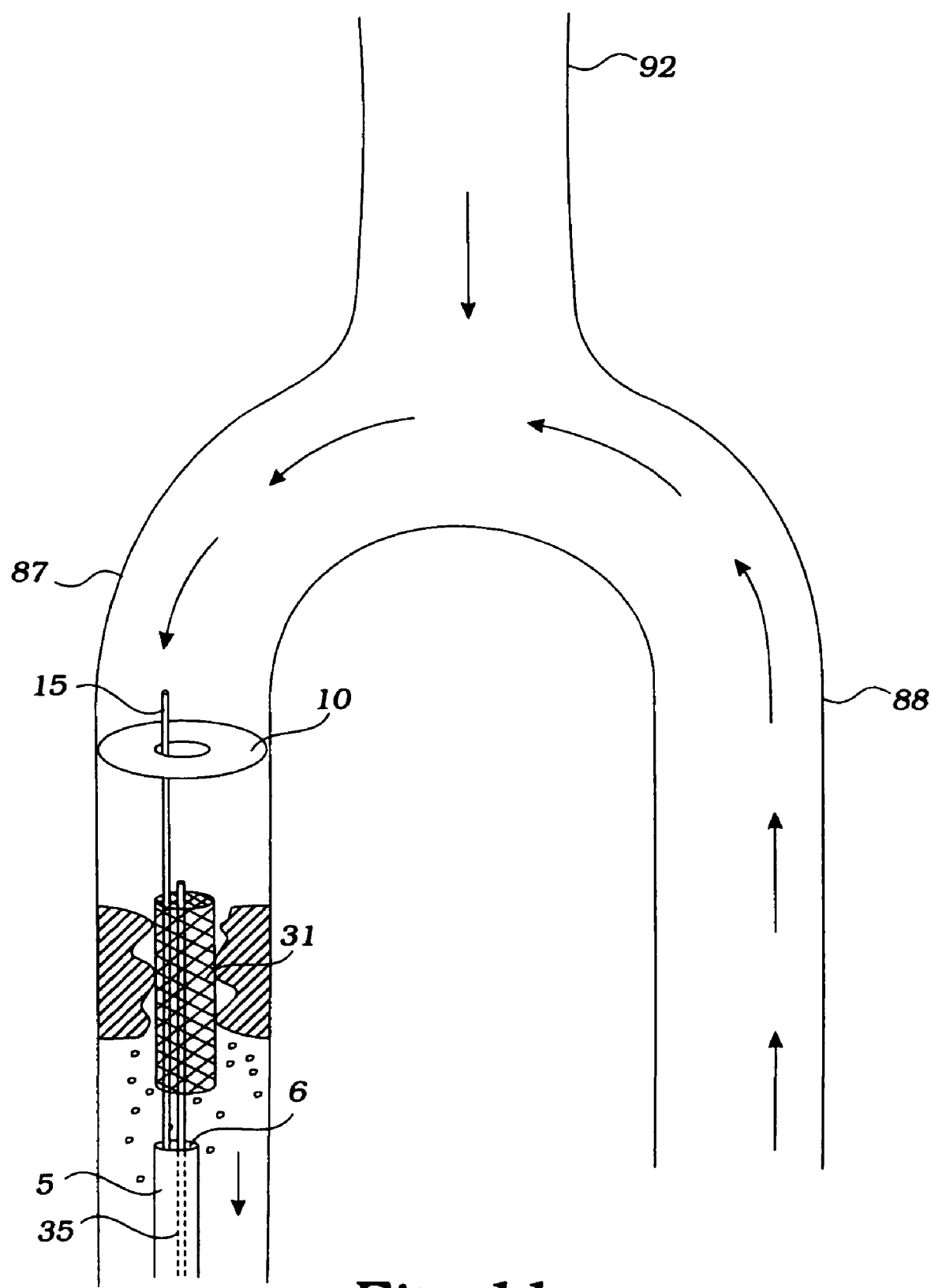
FIG. 11 depicts a stent deployment catheter introduced through the device of FIG. 3B in the right vertebral artery.

In FIG. 11, the distal end of the catheter is inserted in an antegrade fashion in right vertebral artery 87 and advanced across the atheromatous lesion to position distal the lesion. Catheter 30 carrying stent 31 is introduced through lumen 5 and port 6. After flow reversal across the lesion is established by expanding constricting member 10, the stent is deployed over the atheromatous lesion, thereby compressing the lesion and enlarging the lumenal diameter. Compression of the atheroma by the stent often generates embolic debris, including calcium, atheromatous plaque, and thrombi. It will be understood that the interventional therapy may include angioplasty and/or stent deployment and/or atherectomy in every method described herein. With reversal of blood flow in the right vertebral artery, distal embolization to the intracranial cerebral arteries is avoided, thereby minimizing risk of ischemic stroke.

Figure 12:
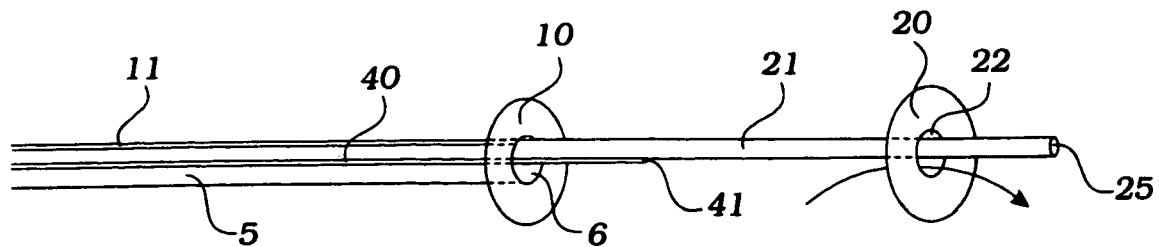
FIG. 12 depicts another embodiment of the device having a proximal occluder and a distal constrictor.

FIG. 12 depicts another embodiment of the device having second lumen 40 communicating with second port 41. The second lumen and port are adapted for delivering a pharmaceutical agent, e.g., tissue plasminogen activator (t-PA), a neuroprotective agent, or an angiographic dye. Local administration of a thrombolytic agent to an occluded vertebral artery reduces the risk associated with systemic thrombolytic therapy, i.e., hemorrhage. Administration of dye through port 41 provides fluoroscopic verification of flow reversal in the vertebral artery.

Figure 13:
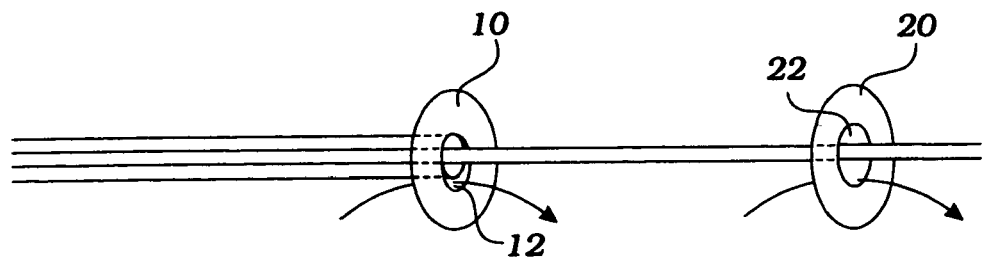
FIG. 13 depicts another embodiment of the device having a proximal constrictor and a distal constrictor.
Figure 14A:
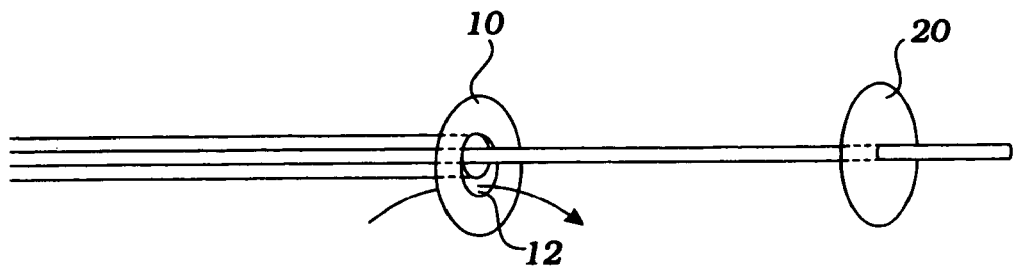
FIG. 14A depicts another embodiment of the device having a proximal occluder and a distal occluder.
Figure 14B:
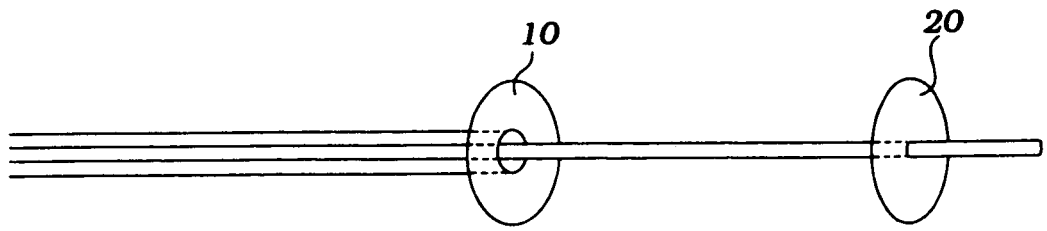
FIG. 14B depicts another embodiment of the device having a proximal occluder and a distal occluder.

FIGS. 12, 13, 14A, and 14B depict alternative devices for use in the inventions described herein. Each catheter has first balloon 10 and second balloon 20. All combinations of constrictors and occluders are contemplated. Thus, first balloon 10 may be an occluder, and second balloon 20 may be a constrictor (FIG. 12). Alternatively, first balloon 10 may be a constrictor, and second balloon 20 may be a constrictor (FIG. 13). Alternatively, first balloon 10 may be a constrictor, and second balloon 20 may be an occluder (FIG. 14A). Alternatively, first balloon 10 may be an occluder, and second balloon 20 may be an occluder (Fig. 14B).

Figure 15A:
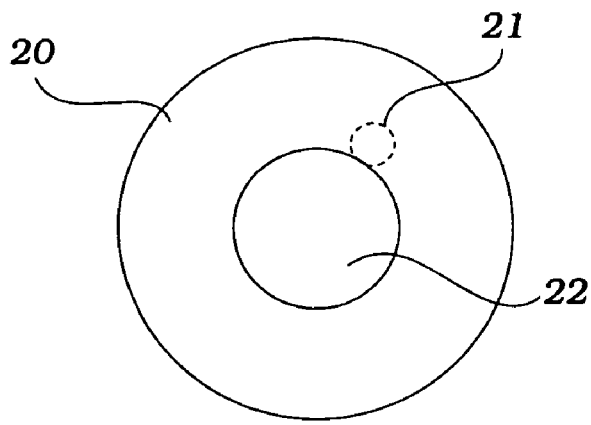
FIG. 15A depicts a cross-sectional view of the constrictor having a central opening for passage of blood.
Figure 15B:
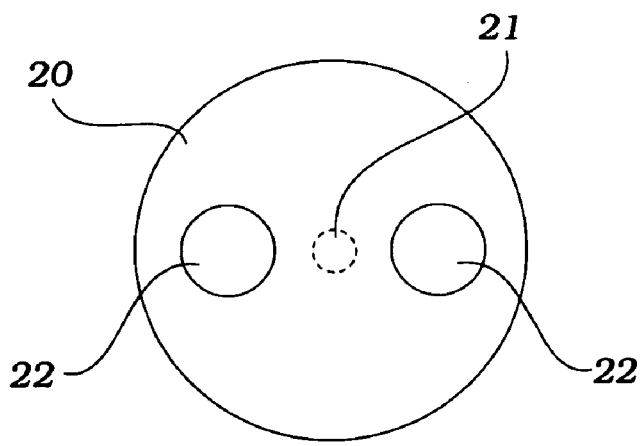
FIG. 15B depicts a cross-sectional view of the constrictor having two openings for passage of blood.
Figure 15C:
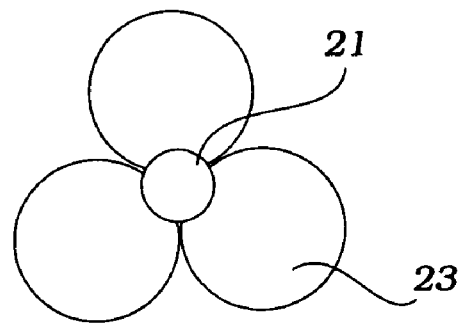
FIG. 15C depicts a cross-sectional view of the constrictor comprising three expandable balloons.

FIGS. 15A, 15B, and 15C depict cross-sectional views of different constructions of the constrictor for allowing blood flow past the constrictor. In FIG. 15A, constrictor 20 is a toroidal balloon which communicates with inflation lumen 21 and includes central opening 22 for passage of blood. In FIG. 15B, balloon constrictor 20 communicates with inflation lumen 21 and communicates with two openings 22 for passage of blood. In FIG. 15C, the constrictor comprises three expandable balloons 23 communicating with inflation lumen 21. When inserted in the subclavian artery, for example, blood passes in the gap between the arterial wall and the expanded balloons. In all three of these designs the constrictor, when expanded, maintains contact with the arterial wall, thus reducing trauma and further emboli dislodgment caused by the balloon impacting the vessel wall by oscillating in the blood flow.

Figure 16A:
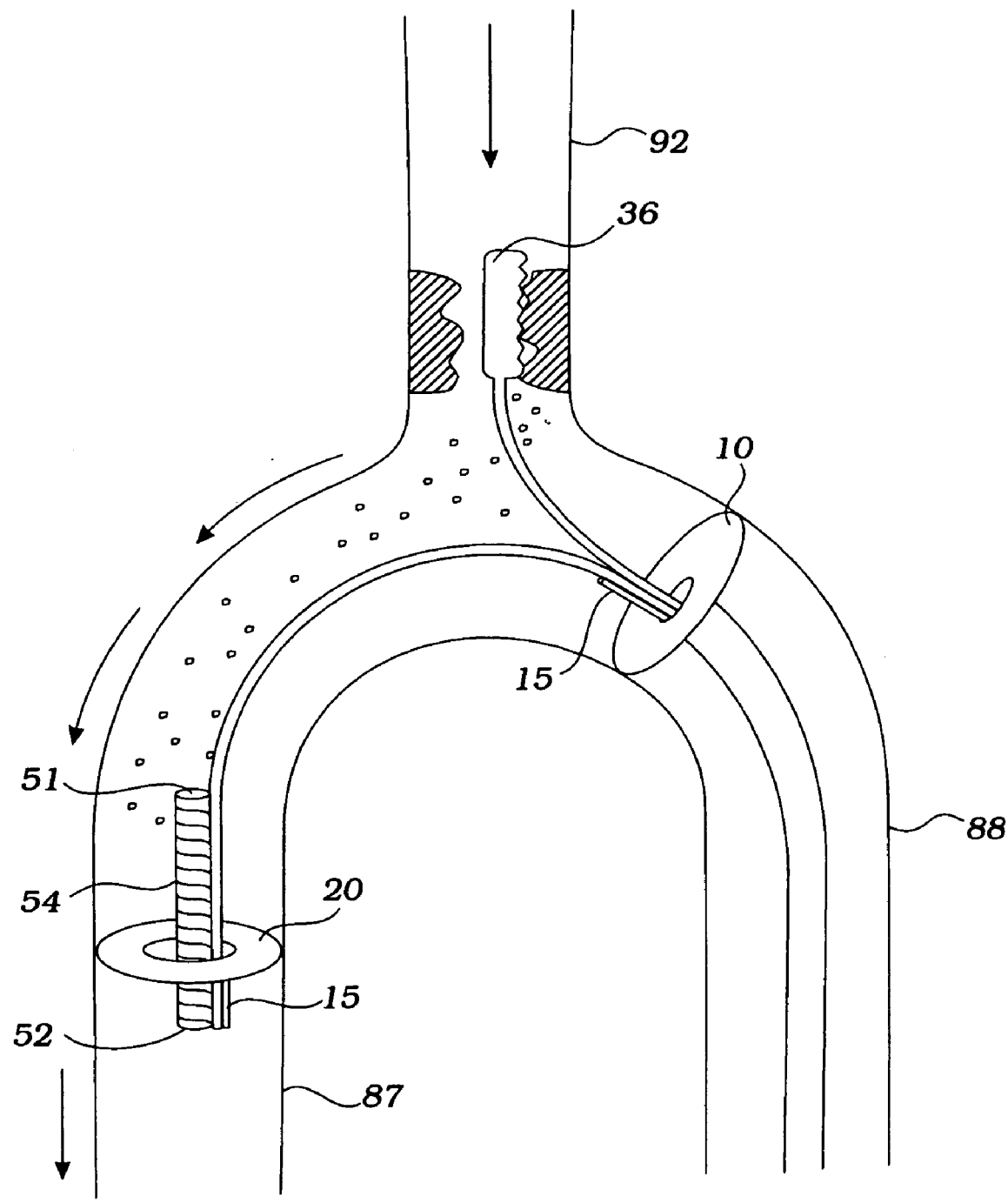
FIG. 16A depicts the device of FIG. 4B inserted in the vertebral arteries for performing atherectomy on an occluding lesion in the basilar artery.

In using the device of FIG. 14B to treat an occluding lesion in the basilar artery, for example, first occluder/constrictor 10 is positioned in left vertebral artery 88, and distal end 52 of the shunt is positioned in right vertebral artery 87 as shown in FIG. 16A. Alternatively, first occluder/constrictor 10 is positioned in right vertebral artery 87, and distal end 52 of the shunt is positioned in left vertebral artery 88. Preferably, the first occluder/constrictor is expanded to occlude the left vertebral artery, followed by expansion of the second occluder/constrictor to constrict the right vertebral artery to cause reversal of blood flow from basilar artery 92 into the right vertebral artery. After flow reversal is established, a therapeutic instrument, such as an atherectomy catheter as depicted in FIG. 16A is introduced through a lumen of the device. Embolic debris generated by atherectomy device 36 is diverted into the right vertebral artery, thereby preventing distal embolization up the brain stem.

Figure 16B:
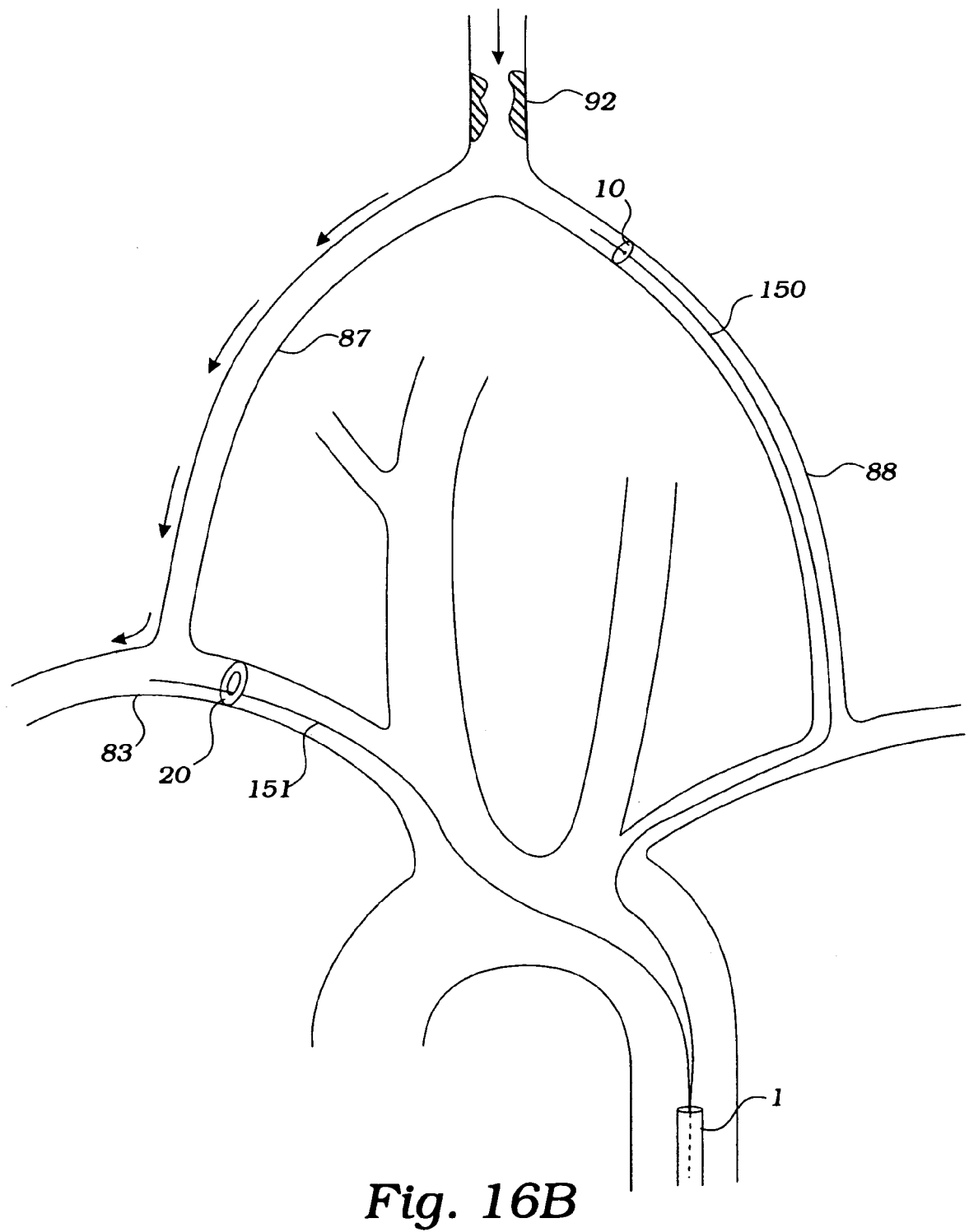
FIG. 16B depicts a medical device having a first constricting/occluding member inserted in the left vertebral artery and a second constricting/occluding member inserted in the right subclavian artery for treating a basilar artery occlusion.
Figure 16C:
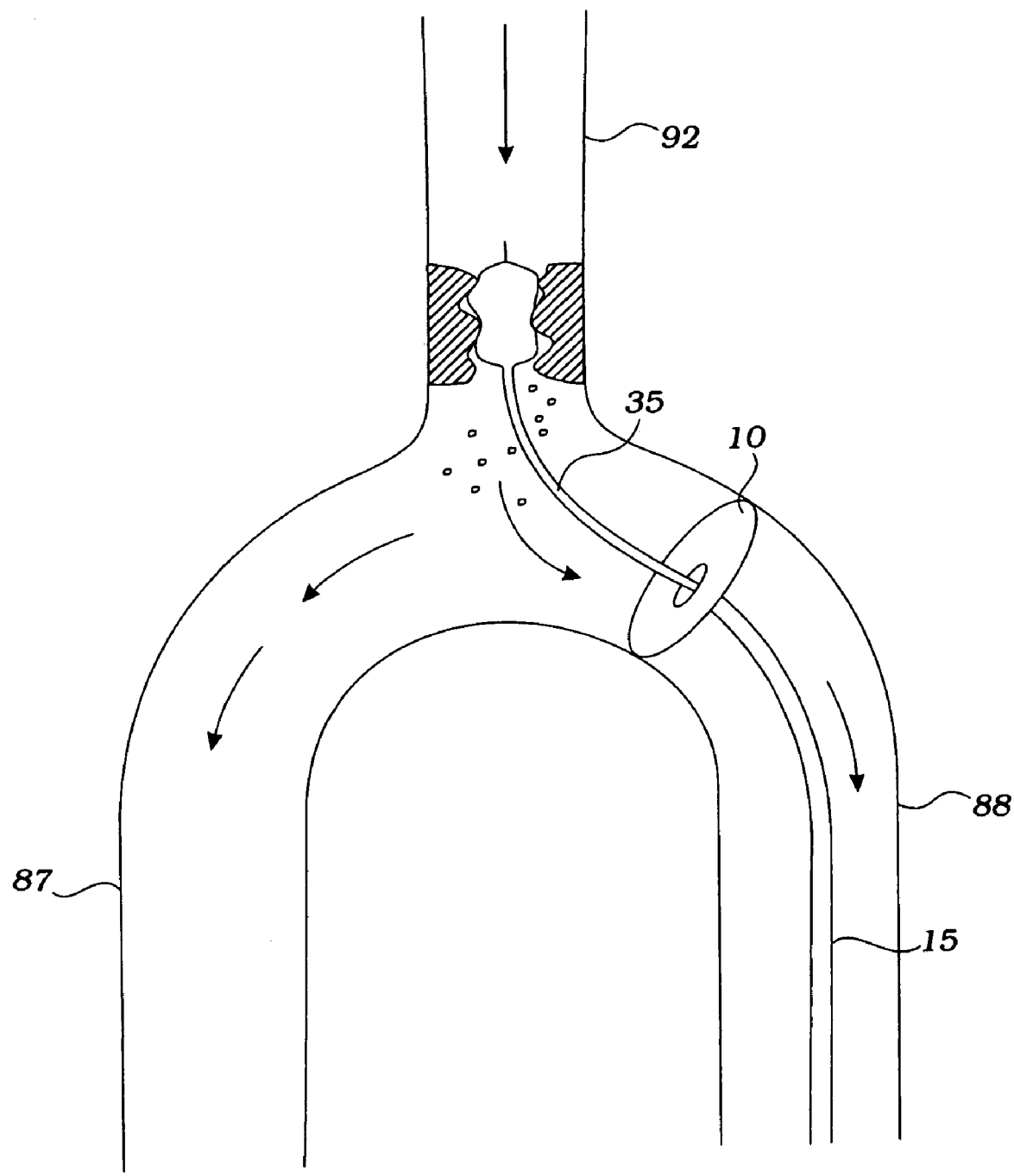
FIG. 16C depicts a medical device having a constricting/occluding member inserted in the left vertebral artery and an angioplasty balloon inserted through the medical device to dilate the basilar artery occlusion.
Figure 16D:
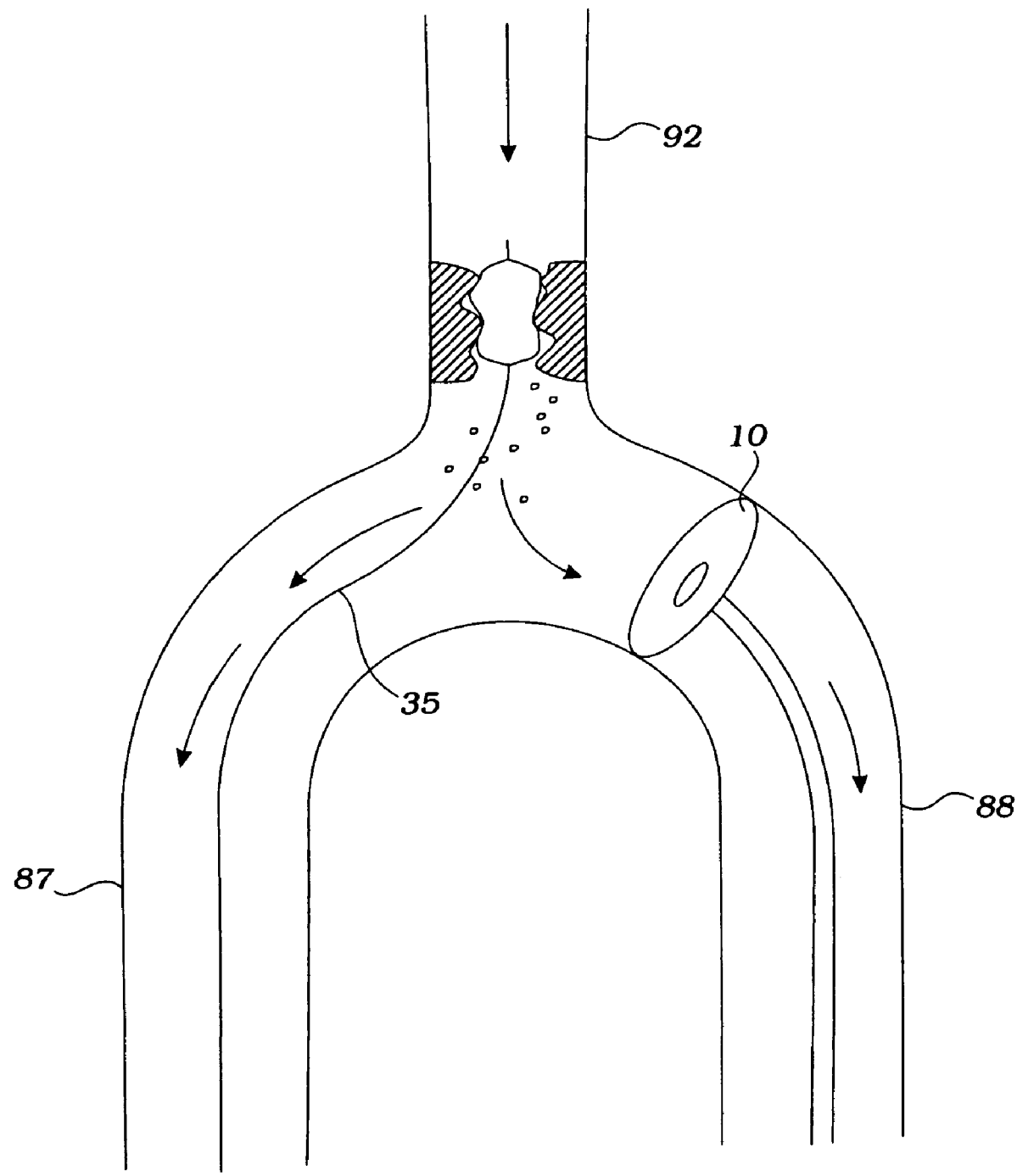
FIG. 16D depicts a medical device having a constricting/occluding member inserted in the left vertebral artery and an angioplasty balloon inserted independent of the medical device to dilate the basilar artery occlusion.
Figure 16E:
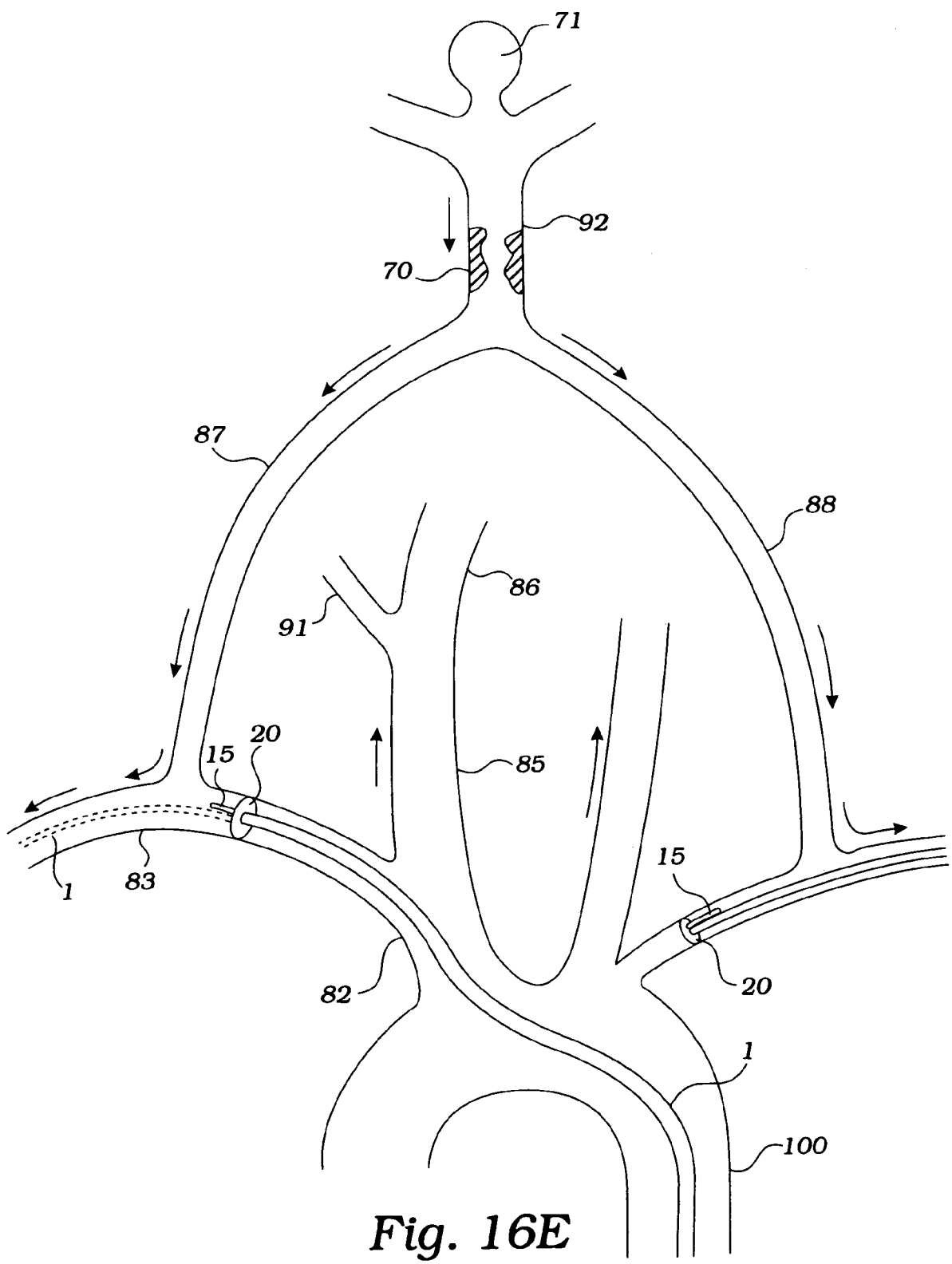
FIG. 16E depicts a medical device having a constricting/occluding member inserted in the left subclavian artery and a second medical device having a constricting/occluding member inserted in the right subclavian artery for causing basilar artery flow reversal.

In treating an occluding lesion in the basilar artery, reversal of blood flow from the basilar artery into the vertebral artery can also be accomplished by inserting a first constricting member in a vertebral artery and a second constricting member in the contralateral subclavian artery upstream the takeoff of the contralateral vertebral artery. Alternatively, first and second constricting members are placed in the right and left subclavian arteries upstream the takeoff of the respective vertebral arteries (FIG. 16E). For example, in FIG. 16B, first constricting member 10 is inserted in an antegrade direction into left vertebral artery 88 through an incision on a peripheral artery, e.g., the femoral artery. Second constricting member 20 is also inserted in an antegrade direction into right subclavian artery upstream the takeoff of right vertebral artery 87. Catheters 150 and 151 which carry, respectively, first and second constricting members 10 and 20 are joined proximally in catheter 1 and are independently operable with respect to each other. Alternatively, the first and second constricting members are introduced independently through separate incisions on the peripheral arteries, e.g., femoral or subclavian (FIG. 16E). Constricting member 10 is then expanded to constrict or occlude the left vertebral artery, causing a pressure drop in the vertebrobasilar junction. If flow reversal from basilar artery 92 into right vertebral artery fails to occur, constricting member 20 is slowly expanded to constrict or occlude the right subclavian artery to further reduce pressure in the right vertebral artery. After flow reversal is established, introduction of therapeutic device(s) into the basilar artery can be achieved through the lumen of catheter 150 (FIG. 16C), or independent of catheter 150 (FIG. 16D). Embolic debris generated during the procedure(s) is diverted from the basilar artery into the right vertebral artery and the right subclavian artery, thereby preventing devastating consequences of brainstem embolization.

Figure 17:
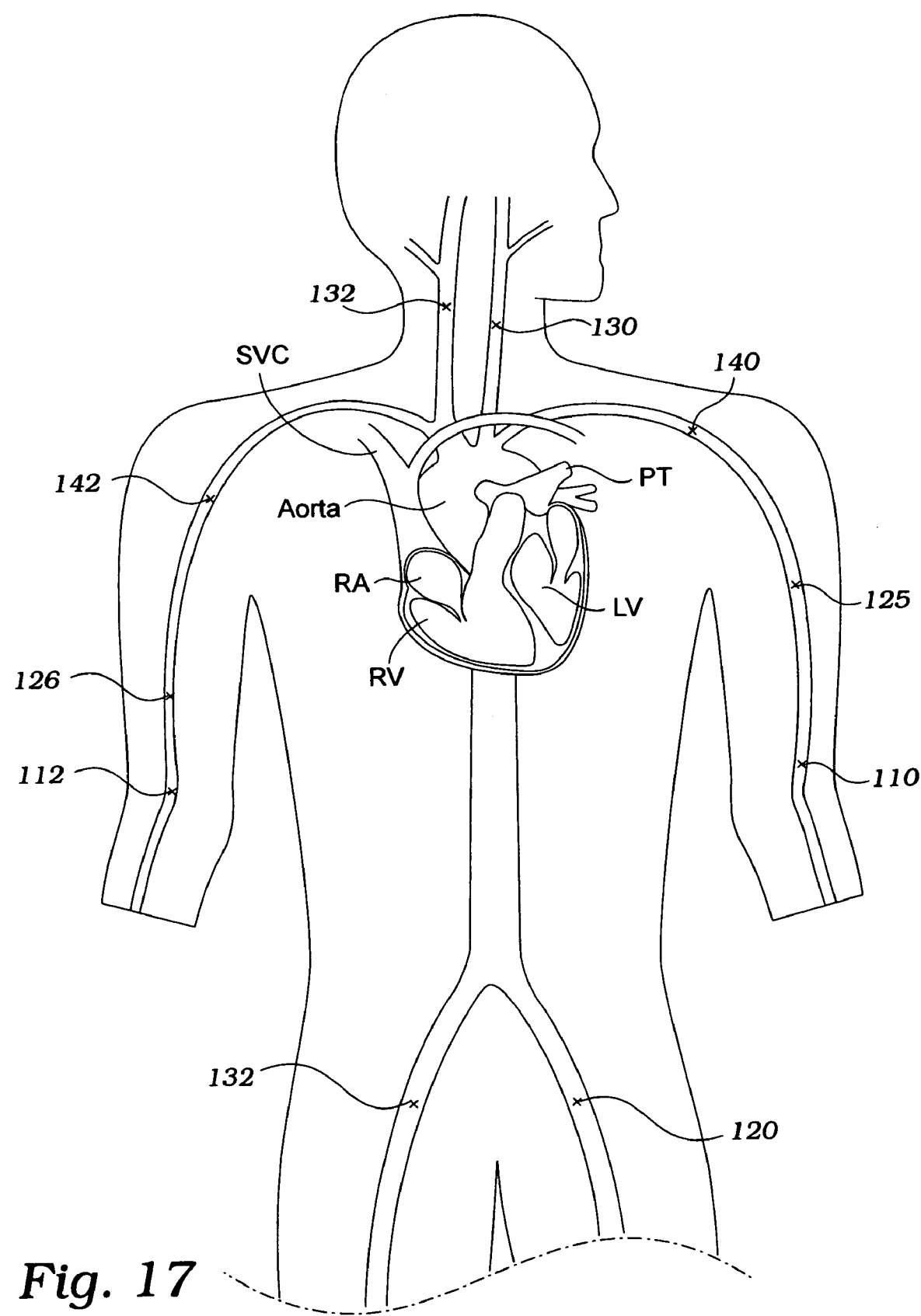
FIG. 17 depicts incision sites on various peripheral arteries for the insertion of the medical device.

FIG. 17 depicts different sites of entry for the devices disclosed herein. An incision can be made on a peripheral artery, such as right femoral artery 122, left femoral artery 120, right brachial artery 112, left brachial artery 110, right axillary artery 126, left axillary artery 115, right subclavian artery 142, or left subclavian artery 140. An incision can also be made on right carotid artery 132 or left carotid artery 130 in emergency situations.

The length of catheter will generally be between 10 and 200 centimeters, preferably approximately between 30 and 150 centimeters. The inner diameter of the catheter lumen will generally be between 0.1 and 0.6 centimeters, preferably approximately between 0.2 and 0.4 centimeters. The diameter of the expanded constrictor/occluder will generally be between 0.3 and 2 centimeters, preferably approximately 0.3 and 0.7 centimeter. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. For example, it will be understood that the features of any particular device or method described herein can be used with any of the other devices or methods described herein.

What is claimed is:

1. A method for treating a vertebral artery lesion, the method comprising the steps of:

inserting a distal end of a catheter into a brachiocephalic trunk, the catheter having a proximal end, the distal end of the catheter having a constricting member;

locating the constricting member at a location in the brachiocephalic trunk upstream a vertebral artery having a lesion;

expanding the constricting member at the location to constrict the brachiocephalic trunk, wherein blood flow in the vertebral artery is reversed to pass over the lesion and toward a subclavian artery; and advancing a therapeutic instrument into the vertebral artery to treat the lesion.

2. The method of claim 1, wherein the lesion is an occlusion or stenosis.

3. The method of claim 1, wherein the lesion is a dissection.

4. The method of claim 1, wherein the catheter is inserted into the brachiocephalic artery in an antegrade direction.

5. The method of claim 1, wherein the vertebral artery is the right vertebral artery.

6. The method of claim 1, wherein the occlusion partially occludes the vertebral artery.

7. The method of claim 1, wherein the occlusion is a stenosis.

8. The method of claim 1, wherein the occlusion is an embolus.

9. The method of claim 1, wherein the occlusion is an atheroma.

10. The method of claim 1, wherein the constricting member is expanded to occlude the brachiocephalic artery.

11. The method of claim 1, wherein the constricting member is expanded to partially occlude the brachiocephalic artery.

12. The method of claim 1, wherein the constricting member is a balloon that communicates with an inflation lumen that extends to the proximal end of the catheter.

13. The method of claim 12, wherein the balloon is a toroidal balloon.

14. The method of claim 1, wherein the therapeutic instrument is an angioplasty catheter.

15. The method of claim 1, wherein the therapeutic instrument is a stent.

16. The method of claim 1, wherein the therapeutic instrument is an atherectomy catheter.

17. The method of claim 1, wherein the catheter has a lumen adapted to pass the therapeutic instrument.

* * * * *